United States Patent [19]
Sandyk

[11] Patent Number: 5,885,976
[45] Date of Patent: *Mar. 23, 1999

[54] METHODS USEFUL FOR THE TREATMENT OF NEUROLOGICAL AND MENTAL DISORDERS RELATED TO DEFICIENT SEROTONIN NEUROTRANSMISSION AND IMPAIRED PINEAL MELATONIN FUNCTIONS

[76] Inventor: Reuven Sandyk, 7 Piper Ct., Roslyn, N.Y. 11576

[ * ] Notice: The term of this patent shall not extend beyond the expiration date of Pat. No. 5,470,846.

[21] Appl. No.: 978,383

[22] Filed: Nov. 25, 1997

Related U.S. Application Data

[63] Continuation-in-part of Ser. No. 437,273, May 8, 1995, Pat. No. 5,691,324.

[51] Int. Cl.⁶ .................................................. A61K 31/60
[52] U.S. Cl. .................... 519/159; 514/160; 514/250; 514/345; 514/355; 514/419; 514/654; 514/657
[58] Field of Search ..................................... 514/159, 160, 514/250, 355, 345, 419, 654, 657

[56] References Cited

U.S. PATENT DOCUMENTS 5,470,846 11/1995 Sandyk ..................................... 514/159
5,691,324 11/1997 Sandyk ..................................... 514/159

Primary Examiner—Richard L. Raymond
Attorney, Agent, or Firm—Graham & James LLP

[57] ABSTRACT

A composition is described which is useful for treating neurological and mental disorders which are associated with and/or related pathogenetically to deficient serotonin neurotransmission and impaired pineal melatonin functions in humans the composition being administered in combination with a sufficient amount of an AC pulsed magnetic field alone or in conjunction with a DC magnetic field and a sufficient amount of random noise to the brain of a human in need of such treatment which composition comprises an effective amount of a composition which increases serotonin transmission to the human to be treated. A method of treating neurological and mental disorders which are associated with and/or related pathogenetically to deficient serotonin neurotransmission and impaired pineal melatonin functions in humans is described which comprises administering to a human in need thereof an effective amount of a composition which increases serotonin transmission to the human to be treated followed by the application to the brain of the human of a sufficient amount of AC pulsed magnetic field alone, or in combination with a DC magnetic field and low frequency random noise, of proper intensity, frequency, waveform, wave symmetry and phase shift of the wave to treat the disorder.

45 Claims, 17 Drawing Sheets

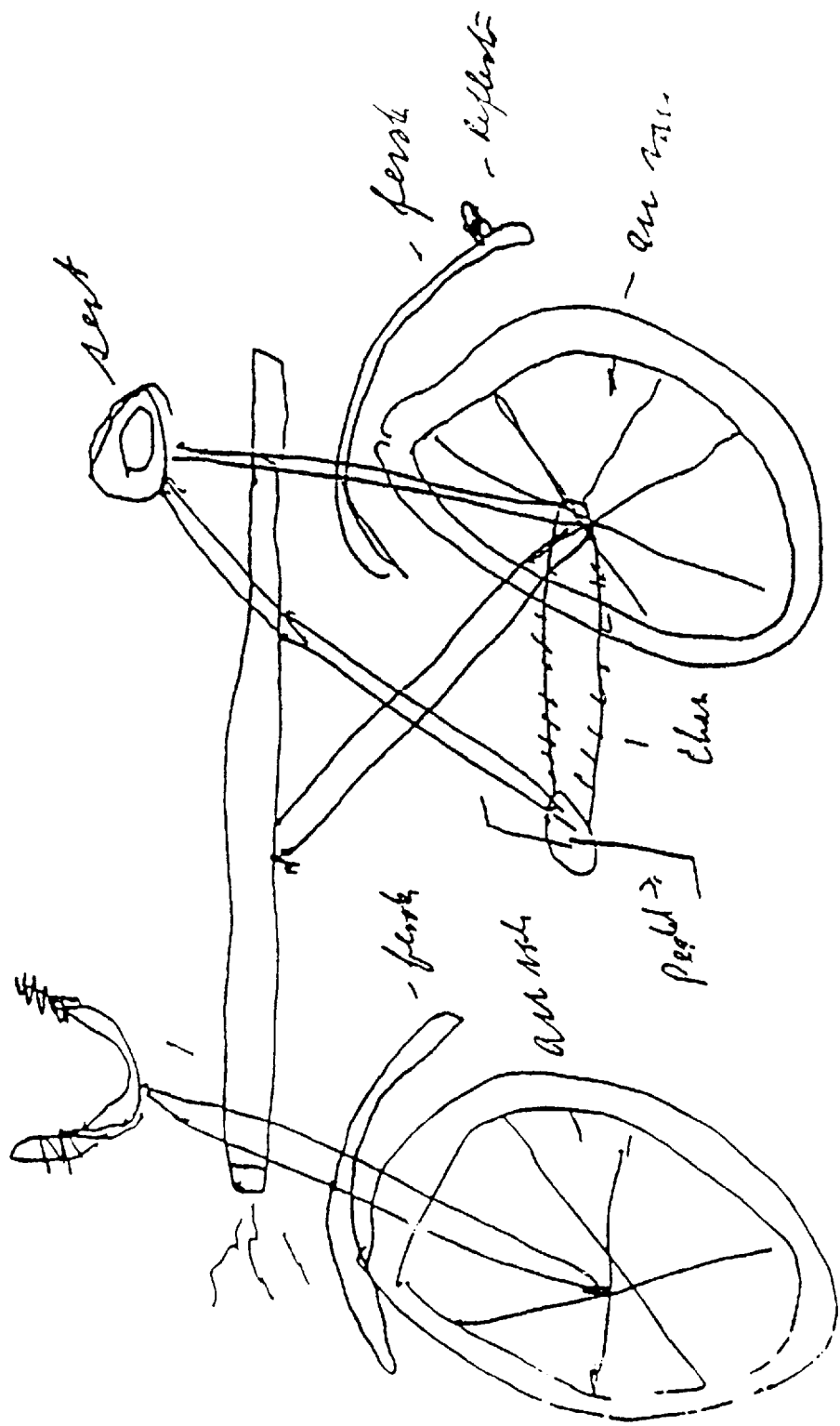
FIG. IC

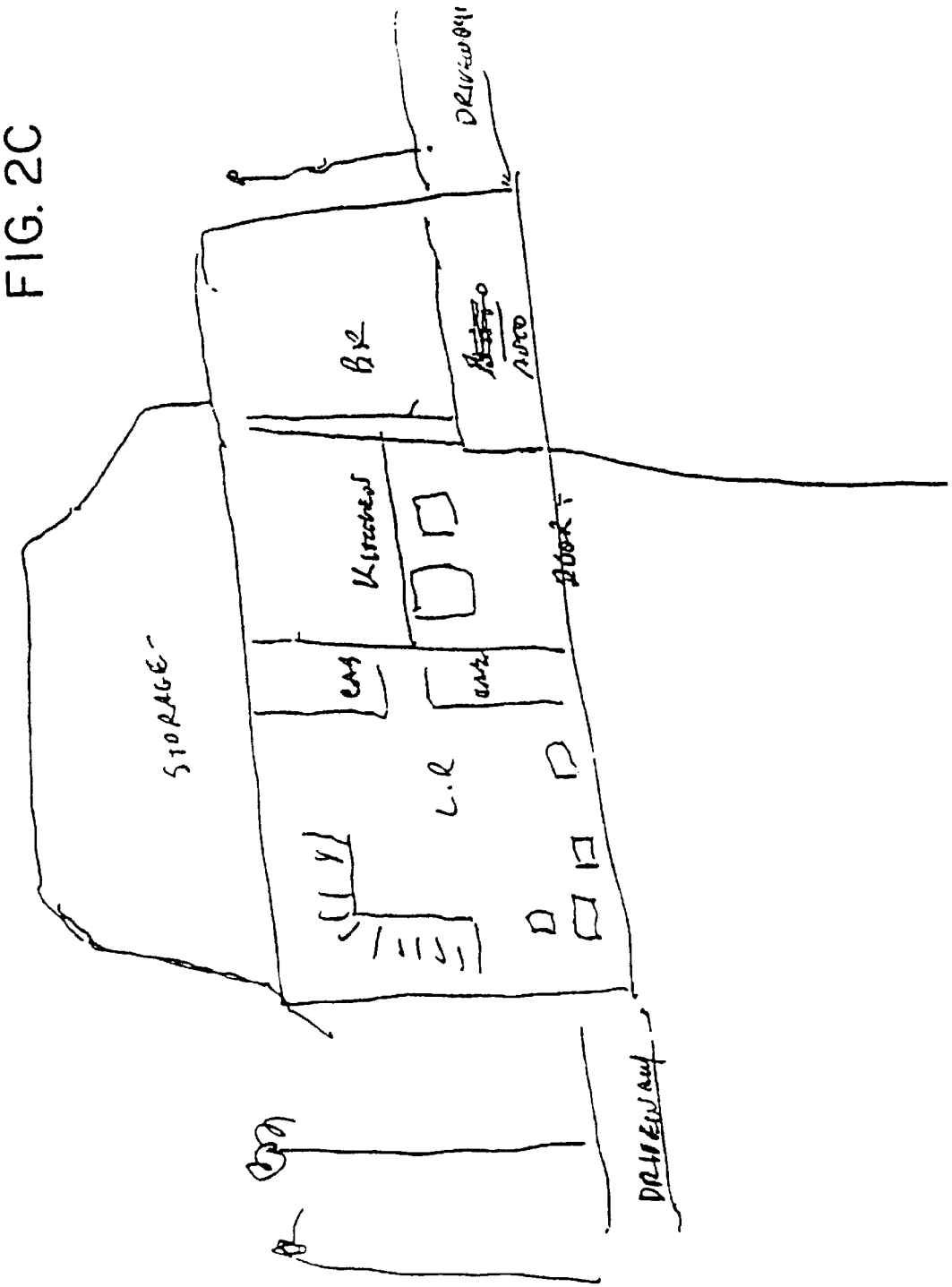

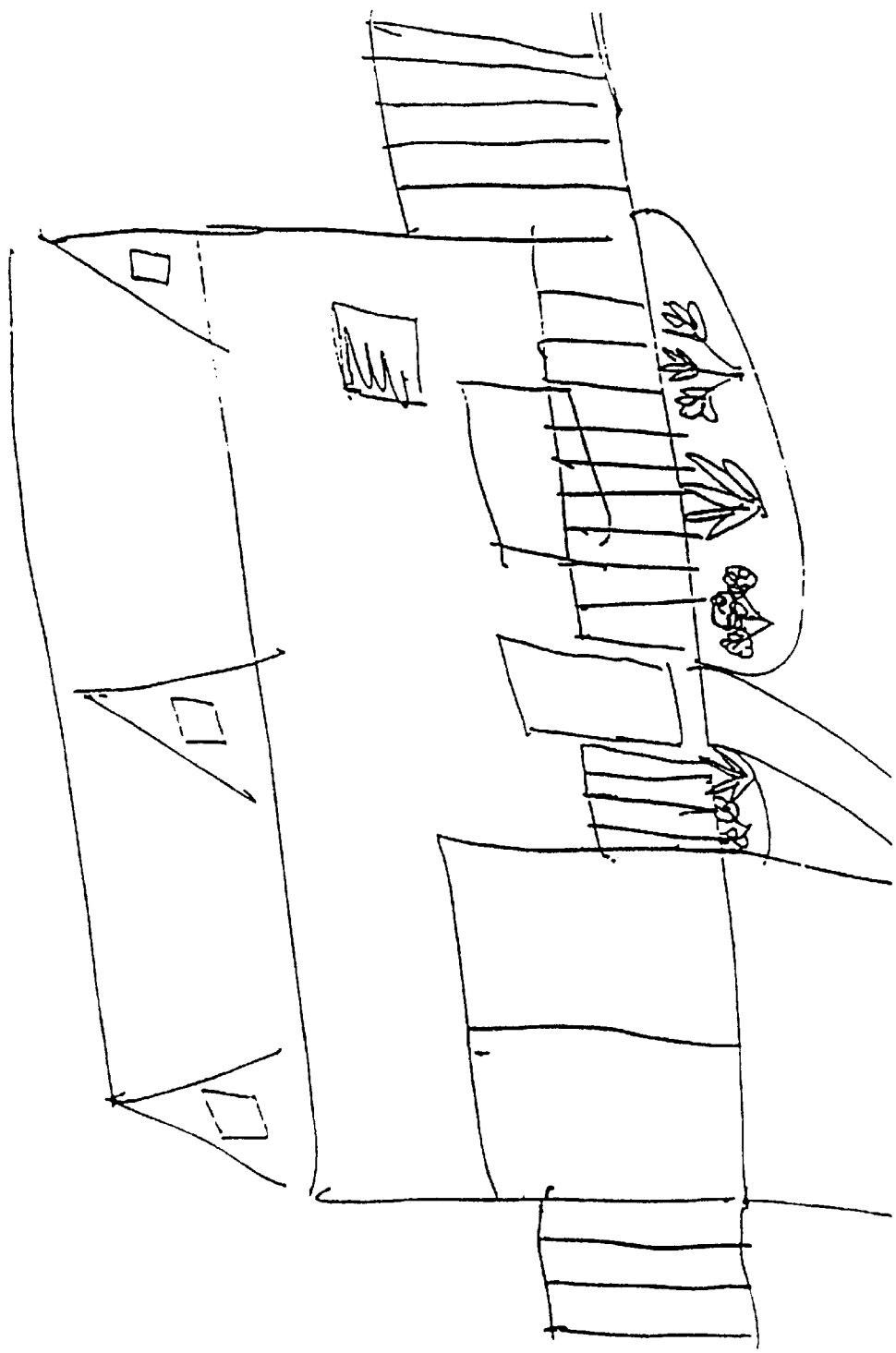

FIG. 4B

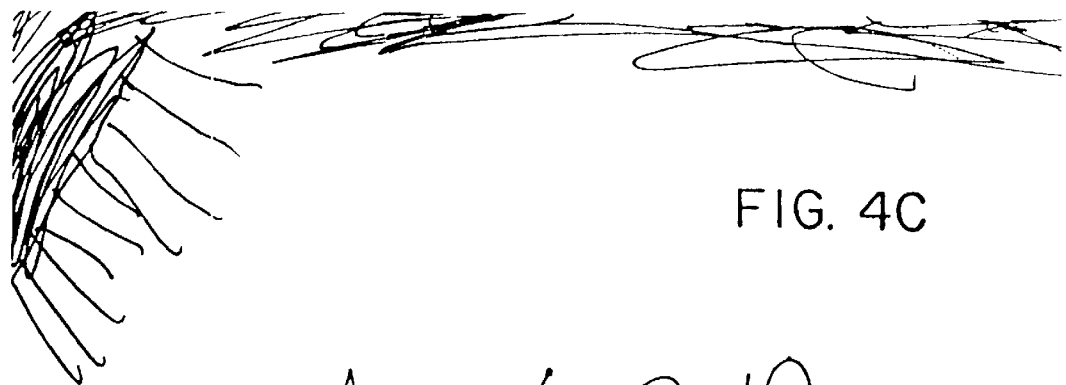
FIG. 4C

FIG. 9
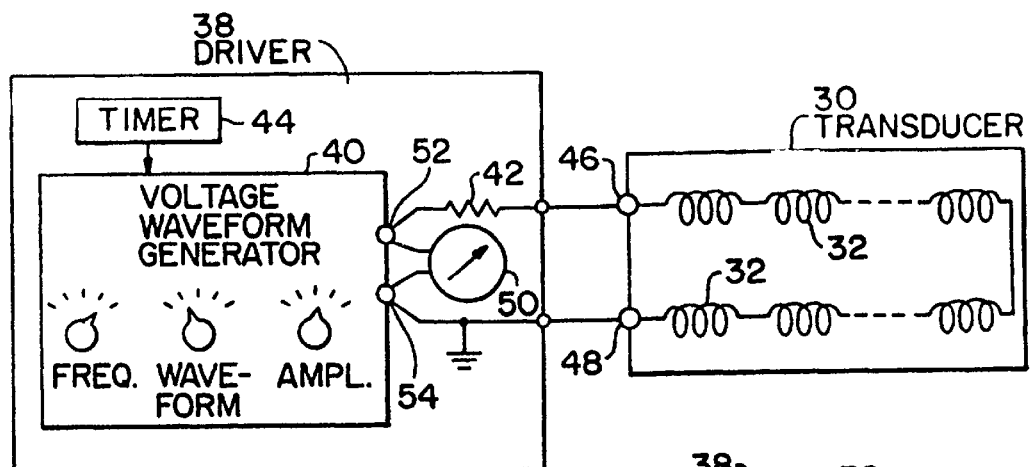
FIG. 10
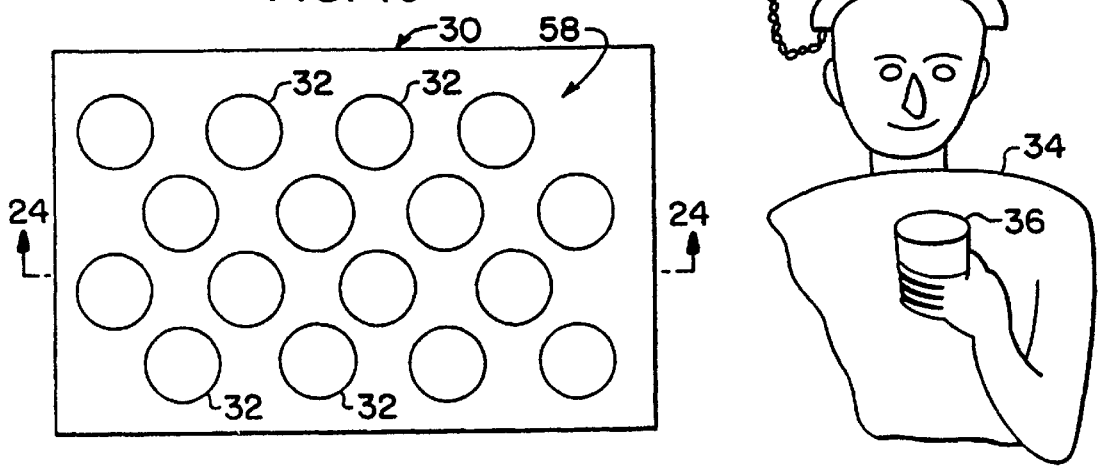
FIG. 12
FIG. 11
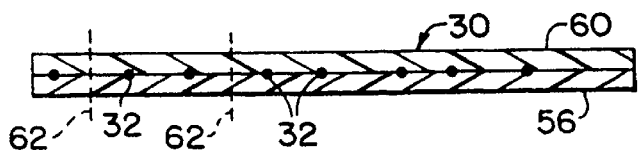
FIG. 10A
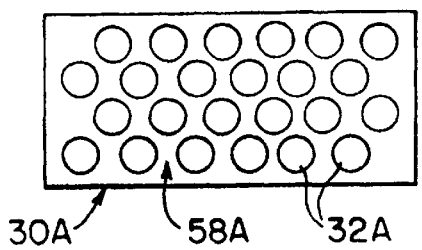

FIG. 13
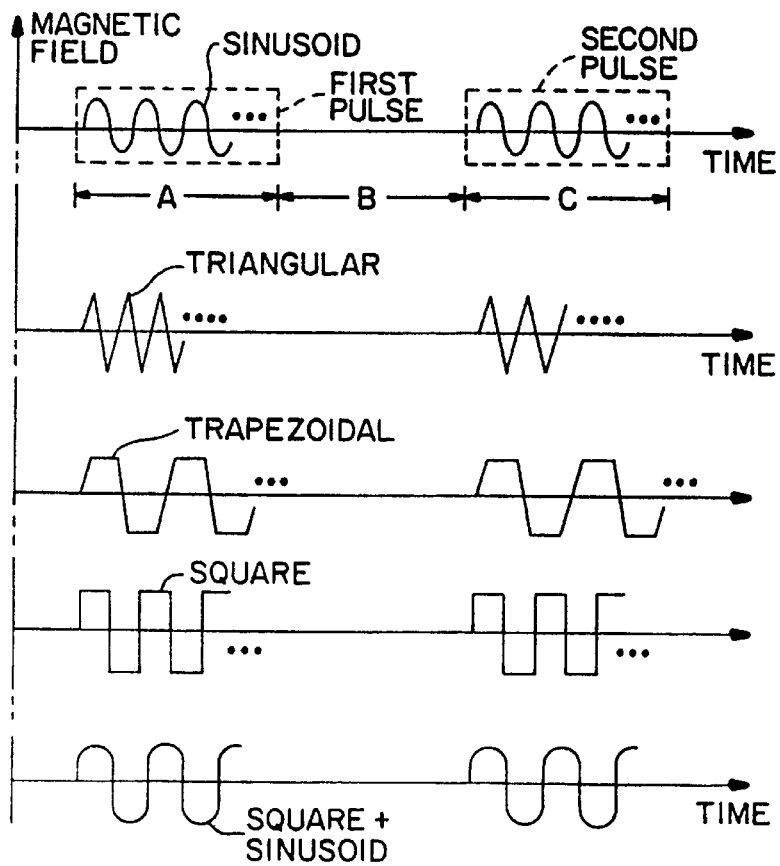
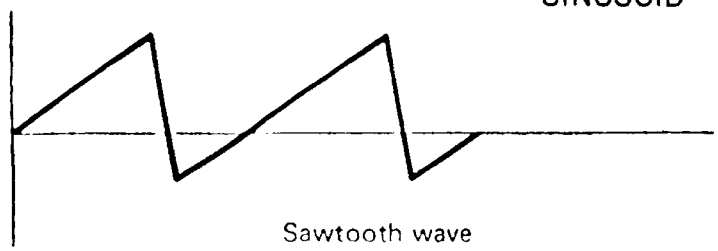
Sawtooth wave
FIG. 14

METHODS USEFUL FOR THE TREATMENT OF NEUROLOGICAL AND MENTAL DISORDERS RELATED TO DEFICIENT SEROTONIN NEUROTRANSMISSION AND IMPAIRED PINEAL MELATONIN FUNCTIONS

This is a continuation-in-part of application Ser No. 08/437,273, filed May 8, 1995, now U.S. Pat. No. 5,691,324.

BACKGROUND OF THE INVENTION

The present invention relates to a method of treating neurological and mental disorders which are associated with and/or related pathogenetically to deficient serotonin neurotransmission and impaired pineal melatonin functions in humans.

The pineal gland serves as a magnetoreceptor organ in the brain of humans and other mammals and its stimulation with an AC pulsed magnetic field has shown beneficial effects in the treatment of neurological and mental disorders which are associated with or related pathogenetically to impairment of pineal melatonin functions including multiple sclerosis, Parkinson's disease, juvenile Parkinsonism, progressive supranuclear palsy. Huntington's chorea, Shy-Drager syndrome, essential tremor, AIDS dementia complex, motor neuron disease, traumatic spinal cord injuries, ischemic stroke, diabetic neuropathy, dystonia, myoclonus, tardive dyskinesia, Tourette's syndrome, epilepsy, narcolepsy, Restless-legs syndrome, akathisia, chronic pain syndromes, migraine, Alzheimer's disease, depression (including seasonal affective disorder and premenstrual depression), autism, Attention Deficit hyperactivity disorder, schizophrenia, alcohol and substance abuse, obsessive-compulsive disorder, anxiety and panic disorder, posttraumatic stress disorder, trichotillomania, impulsive and aggressive behavior, chronic insomnia, sleep paralysis, and bulimia.

For many years physiologists considered the pineal gland, lodged deep within the brain, a vestigial organ which is merely an anatomical remnant of a primary sensory system. To the clinician the pineal gland, by virtue of its midline position and calcification, was of interest as a radiological landmark to identify intracranial space occupying processes. The pineal gland attracted scientific attention in 1963, when its primary secretion, melatonin, was first recognized as a hormone. Wurtman and Axelrod (1965) "The pineal gland." *Scientific American,* 231, 50–60) considered the pineal gland a "neuroendocrine transducer," an organ which converts neural signals from the external environment such as photic, acoustic, thermic, and magnetic cues into neuroendocrine output which acts on the nervous system largely via the secretion of its principal hormone melatonin. The pineal gland is unique among endocrine organs for a number of reasons: (1) it is one of the few unpaired endocrine organs; (2) on a weight basis, it receives one of the richest blood supplies of any organ; (3) it lies outside the blood brain barrier, but has direct access to the cerebrospinal fluid (CSF) via the third ventricle; (4) it produces and/or contains high concentrations of a number of different indoleamines and low molecular weight peptides of probable endocrine importance; and (5) it is responsive to changes in magnetic field strength and to external electrical stimuli (Foley et al., (1986) "Pineal indoles: significance and measurement." *Neuroscience & Biobehavioral Reviews,* 10, 273–293).

Over the post several years scientists have come to suspect that melatonin could be a "master hormone" involved in the control of circadion rhythms (biological cycles that recur at approximately 24-hour intervals), and protecting against some of the common diseases of aging through its free radical scavenging effects (Daniels et al., (1996) "Free radical scavenging effects of melatonin and serotonin: possible mechanism." *NeuroReport,* 7, 1593–1596). Melatonin is now recognized to exert an important influence on a host of biological functions including synchronization of biological rhythms, stabilization of neuronal activity, regulation of sexual maturation and reproduction, immunomodulation, temperature control, sleep, mood, pain control, cognitive functions, and motor behavior (Ehrlich and Apuzzo (1985) "The pineal gland: anatomy, physiology, and clinical significance." *Journal of Neurosurgery,* 63, 321–341; Miles and Philbrick (1988) "Melatonin and Psychiatry." *Biological Psychiatry,* 23, 405–425; Romijn (1978). "The pineal, a tranquillizing organ?" *Life Sciences,* 23, 2257–2274; Lakin et al., (1981) "Involvement of the pineal gland and melatonin in murine analgesia." *Life Sciences,* 29, 2543–2551; Kavaliers et al., (1983) "Ageing, opoid analgesia and the pineal gland." *Life Sciences,* 32, 2279–2287; Cotzias et al., (1971) "Melatonin and abnormal movement induced by L-dopa in mice." *Science,* 173, 450–452; Reiter (1991) "Pineal melatonin: cell biology of its synthesis and of its physiological interactions." *Endocrine Reviews,* 12, 151–180; Brzezinski (1997) "Melatonin in humans," *New England Journal of Medicine,* 336, 186–195).

Many of the biological effects of melatonin result from its action on serotonergic neurons indicating that the neurotransmitter serotonin is an important mediator of melatonin's biological actions and that deficient serotonin neurotransmission may disrupt melatonin's biological functions (Anton-Tay et al., (1968) "Brain serotonin concentration: elevation following intraperitoneal administration of melatonin." *Science,* 162, 277–278; Gaffori and Van Ree (1985) "Serotonin and antidepressant drugs antagonize melatonin-induced behavioral changes after injection into the nucleus accumbens of rats."*Neuropharmacology,* 24, 237–244: Namboodiri et al., (1983) "5-hydroxytryptophan elevates serum melatonin." *Science,* 221, 659–661; Aldegunde et al., (1985) "Effects of pinealectomy on regional brain serotonin metabolism." . *International Journal of Neuroscience,* 26, 9–13; Sugden and Morris (1979) "Changes in regional brain levels of tryptophan, 5-hydroxytryptamine and 5-hydroxyindoleacetic acid, dopamine and noradrenaline after pinealectomy in the rat." *Journal of Neurochemistry,* 32, 1593–1594; Olcese (1985) "Enhancement of melatonin's antigonadal action by daily injections of the serotonin uptake inhibitor fluoxetine in male hamsters." *Journal of Neural Transmission,* 64, 151–161; Smythe and Lazarus (1974) "Growth hormone responses to melatonin in man." *Science,* 184, 1373; Koulu and Lamrmintausta (1979) "Effect of melatonin on L-tryptophan and apomorphine-stimulated growth hormone secretion in man." *Journal of Clinical Endocrinology & Metabolism,* 49, 70–72; Dugovic et al., (1989) *Melatonin modulates the sensitivity of* 5-hydroxytryptophan-2-receptor mediated sleep wakefullness in the rat. *Neuroscience Letters,* 104, 320–325; Miguez et al., (1996) "Changes in serotonin level and turnover in discrete hypothalamic nuclei after pinealectomy and melatonin administration to rats." *Neurochemistry International,* 29, 651–658).

Melatonin production has been shown to change across the lifespan, peaking in childhood and gradually decreasing after puberty. The gradual decline in the secretory activity of the pineal gland after puberty has been linked with the process of aging as melatonin is thought to counteract the deleterious effects of oxygen free radicals—unstable molecules thought to play an important part in atherosclerosis and other diseases associated with aging (Nair et al., (1986) "Plasma melatonin—an index of brain aging in humans?" *Biological Psychiatry*, 21, 141–150; Sack et al., (1986) "Human melatonin production decreases with age." *Journal of Pineal Research*, 3, 379–388; Armstrong and Redman (1991) "Melatonin: a chronoblotic with antiaging properties?" *Medical Hyotheses*, 34, 300–309).

Impaired pineal melatonin function has been implicated in the pathophysiology of numerous systemic, neurological and mental disorders including cancer, autoimmune disorders (i.e., rheumatoid arthritis, systemic lupus), AIDS, diabetes mellitus, hyper-cholesterolemia, mental depression including seasonal affective disorder (SAD), schizophrenia, autism, panic disorder, obsessive compulsive disorder, trichotillomania, substance abuse including alcoholism, posttraumatic stress disorder, impulsive and aggressive behavior, chronic insomnia, sleep paralysis, bulimia, Parkinson's disease, juvenile Parkinsonism, Shy-Drager syndrome, progressive supranuclear palsy (PSP), Huntington's chorea, AIDS dementia, Alzheimer's disease, Korsakoffs dementia, tardive dyskinesia, chronic pain syndromes, diabetic neuropathy, epilepsy, narcolepsy, migraine, multiple sclerosis, ischemic stroke, motor neuron disease, traumatic spinal cord injuries and macular degeneration. These diseases are associated either with deficient melatonin production and/or disruption of melatonin circodian rhythmicity associated with deficient or dysregulated serotonin neurotransmission as disclosed in Anton-Tay et al., (1971) "On the effects of melatonin upon human brain. Its possible therapeutic implications." *Life Sciences*, 10, 841–850; Smith et al., (1978) "Decrease in human serum melatonin concentrations with age." *Journal of Neural Transmission*, 13 (Suppl), 396; Pavel et al., (1980) "Vasotocin, melatonin and norcolepsy: possible involvement of the pineal gland in its pathophysiological mechanism." *Peptides*, 1, 281–284; Martin et al., (1984) "Decreased 6-hydroxymelatonin excretion in Korsakoff's psychosis." *Neurology*, 34, 966–968; Fanget et al., (1989) "Nocturnal plasma melatonin levelsin schizophrenic patients" *Biological Psychiatry*, 25, 499–501; Skene et al., (1990) "Daily variation in the concentration of melatonin and 5-methoxytryptophol in the human pineal gland: effect of age and Alzheimer's disease." *Brain Research*, 528, 170–174; Souetre et al., (1989) "Abnormal melatonin response to 5-methoxypsoralen in dementia." *American Journal of Psychiatry*, 146, 1037–1040; Renfrew et al., (1987) "Circadian rhythms in Alzheimer's disease." *Neurosciences Abstracts*, 1, 322; Armstrong and Redman (1991) "Melatonin: a chronobiotic with antiaging properties?" *Medical Hypotheses*, 34, 300–309; Nair et al.. (1986) "Plasma melatonin—an index of brain aging in humans?" *Biological Psychiatry*, 21, 141–150: Tohgi et al., (1992) "Concentrations of serotonin and its related substances in the cerebrospinal fluid in patients with Alzheimer-type dementia." *Neuroscience Letters*, 141, 9–12: Ferti et al., (1991) "Circadian secretion pattern of melatonin in Parkinson's disease." *Journal of Neural transmission*, 3, 41–47: Ferti et al., (1993) "Circadian secretion pattern of melatonin in de novo Parkinsonian patients: evidence for phase-shifting properties of l-dopa." *Journal of Neural Transmission (P–D Sect)*, 5, 227–234: Sandyk (1992) "The pineal gland and the clinical course of multiple sclerosis." *International Journal of Neuroscience*, 62, 65–74; Sandyk (1992) "The pineal gland and multiple sclerosis." (Editorial) *International Journal of Neuroscience*, 63, 206–215: Toglia, J. U. (1986) "is migraine due to a deficiency of pineal melatonin"? *Italian Journal of Neurological Sciences*, 7, 319–32; Sandyk and Kay (1990) "Pineal melatonin in schizophrenia: a Review and hypothesis." *Schizophrenia Bulletin*, 16, 653–662; Sandyk et al., (1990) "Pineal gland calcification and tordive dyskinesia." *Lancet*, 335, 1528; Robinson et al., (1991) "Serum melatonin levels in schizophrenic and schizoaffective hospitalized patients." *Acta Psychiotrica Scandinavica*, 84, 221–224; Miles and Philbrick (1988) "Melatonin and Psychiatry." *Biological Psychiatry*, 23, 405–425; Nir et al., (1969) "Changes in the electrical activity of the brain following pinealectomy." *Neuroendocrinology*, 4, 122–127; Philo (1982) "Catecholamines and pinealectomy-induced convulsions in the gerbil (*Merinos unguiculatus*)." *Progress in Clinical Biological Research*, 92, 233–241; Reiter et al., (1973) "Nature and time course of seizures associated with surgical removal of the pineal gland from parathyroldectomized rats." *Experimental Neurology*, 38, 386–397; McIntyre et al., (1990) "Plasma concentrations of melatonin in panic disorder." *American Journal of Psychiatry*, 147, 462–464; Moteleone et al. (1994) "Circadian rhythms of melatonin, cortisol and prolactin in patients with obsessive compulsive disorder." *Acta Psychiatrica Scandinavica*, 89, 411–415; Catapano et al., (1992) "Melatonin and cortisol secretion in patients with primary obsessive compulsive disorder." *Psychiatry Research*, 44, 217–225; Sandyk and Kay (1991) "Concordance of Tourette's syndrome and bipolar disorder: possible role of the pineal gland." *International Journal of Neuroscience*, 58, 235–240; Sandyk and Kay (1991) "Pineal melatonin secretion during puberty: possible relevance to Giles de la Tourette's syndrome." *International Journal of Neuroscience*, 58, 232–235; Molina-Carballo et al., (1994) "Day-night variations in melatonin secretion by the pineal gland during febrie and epileptic convulsions in children." *Psychiatry Research*, 52, 273–283; Waldhauser et al., (1993) "Clinical aspects of the melatonin action: impact of development, aging and puberty, involvement of melatonin in psychiatric disease and importance of neuroimmunoendocrine interactions." *Experientia*, 49, 671–681; Brambilla et al., (1988) "Melatonin circadion rhythm in anorexia nervosa and obesity." *Psychiatry Research*, 23, 267–276; Pierpaoli and Regelson (1995) "The melatonin miracle." (pp. 175–177). New York: Pocket Book; Relter (1995) "Melatonin." (pp. 60–72). New York: Bantam Books; Norden (1995) "Beyond prozac." (pp. 8–10). New York: Regan Books; McEntee and Crook (1991) "Serotonin, memory, and the aging brain." *Psychopharmacology*, 103, 143–149; Lawlor (1990) "Serotonin and Alzheimer's disease." *Psychiatric Annals*, 20, 567–570; Comings (1990) "Serotonin and human behavior" In D. E. Comings (Ed.), *Tourette syndrome and human behavior* (pp. 429–444). Duarte: Hope Press; Erlich and Apuzzo (1985) "The pineal gland: anatomy, physiology, and clinical significance." *Journal of Neurosurgery*, 63, 321–341; Sandyk and Fisher (1988) "Serotonin in involuntary movement disorders." *International Journal of Neuroscience*, 42, 185–205; Fuller (1992) "Clinical applications of 5-HT uptake inhibitors." In P B Bradley et al. (Eds.), *Advances in the Biosciences: serotonin, CNS receptors and brain function*, vol. 85 (pp. 255–270); Weingartner et al., (1983) "Effects of serotonin on memory impairments produced by ethanol." *Science*, 221, 472–473; Amit et al., (1984) "Zimeildine: a review of its effects on ethanol consumption." *Neuroscience & Biobehavioral Reviews*, 8, 35–54; Meara (1996) "Serotonin and the extrapyramidal system—a neurological perspective." *Human Psychopharmacology*. 11, S95–S102; Hubble et al., (1989) "Essential tremor." *Clinical Neuropharmacology*, 12, 453–482; Kulmann et al., (1995) "Lack of light/dark rhythm of the pineal hormone melatonin in autistic children." *First International Congress of Clinical Neuroimmunomodulation,* Monza, Italy; Young et al, (1982) "Clinical neurochemistry of autism and associated disorders." *Journal of Autism and Developmental Disorders,* 12, 147–165; Johonsson and Roos (1974) "5-hydroxyindoleacetic acid and homovanillic acid in cerebrospinal fluid of patients with neurological disorders." *European Neurology,* 11, 37–45; Barbeau (1969) "L-dopa and Juvenile Huntington's disease." *Lancet,* 2, 1066; Klawans (1970) "A pharmacologic analysis of Huntington's chorea." *European Neurology,* 4, 148–163; Brody et al., (1970) "Depressed monoamine catabolite levels in cerebrospinal fluid of patients with parkinsonian dementia of Guam" *New England Journal of Medicine,* 232, 947–950; Vaughan et al., (1979) "Melatonin, pituitary function and stress in humans." *Psychoneuroendocriноloy,* 4, 351–362; Tetsuo et al., (1981) "Urinary b-hydroxymelatonin excretion in patients with orthostatic hypotension." *Journal of Clinical Endocrinology and Metabolism,* 53, 607–610; Snyder and llams (1982) "Serotoninergic agents in the treatment of isolated sleep paralysis." *American Journal of Psychiatry,* 139, 1202–1203; Anden et al., (1965) "5-hydroxyindoleacetic acid in rabbit spinal cord normally and after transection." *Acta Physiologica Scandinavica,* 64, 193–196; Brun et al., (1971) "Studies of the monoamine metabolism in the central nervous system in one patient with Jakob Creutzfeldt disease." *Acta Neurologica Scandinavica,* 47, 642–645; Kneisley et al., (1978) "Cervical spinal cord lesions disrupt the rhythm in human melatonin excretion." *Journal of Neural Transmission,* 13 (suppl), 311–323; Li et al., (1989) "Rhythms of serum melatonin in patients with spinal lesions at the cervical, thoracic or lumbar region." *Clinical Endocrinology,* 30, 47–56; Wetterberg (1978) "Melatonin in humans, Physiological and clinical studies." *Journal of Neural Transmission,* 13 (suppl) 289–310; Rojdmar et al., (1993) "Inhibition of melatonin secretion by ethanol in man." *Metabolism,* 42, 1047–1051; Pang et al., (1990) "Acute cerebral haemorrhage: changes in nocturnal surge of plasma melatonin in humans." *Journal of Pineal Research,* 9, 193–208; Manev et al., (1996) "Increased brain damage after stroke or excitotoxic seizures in melatonin-deficient rats." *FASEB Journal,* 10, 1546–1551). Moreover, recent studies have indicated that pineal melatonin exerts an important neuroprotective effect as melatonin deficient animals demonstrate increased vulnerability to cerebral damage after sustaining a focal ischemic/stroke or epileptic-like seizures (Giusti et al., 1995) "Melatonin protects primary cultures of cerebellar granule neurons from kainate but not from N-methyl-D- aspartate excitoxicity." *Experimental Neurology,* 131, 39–46; Manev et al., (1996) "Increased brain damage after stroke or excitotoxic seizures in melatonin-deficient rats." *FASEB Journal,* 10, 1546–1551). These studies suggest that melatonin deficiency reflects a pathophysiological mechanism in neurodegenerative diseases.

The pineal gland is a neural structure that is functionally related to the visual system. Indeed, the circadian production of melatonin is determined by the photoperiodic environment to which animals are exposed. Bright light suppresses pineal melatonin synthesis and secretion while ambient darkness stimulates the production and secretion of the hormone. The effects of the environmental illumination on the pineal gland are mediated via a well-delineated retinohypothalamic-pineal circuit. The rhythms of melatonin secretion are generated by the paired suprachlasmatic nuclei (SCN) of the hypothalamus which serve as the body's biological clock. Serotonin concentrations are higher in the pineal than in any other organ or in any brain region. They exhibit a striking diurnal rhythm, remaining at a maximum level (in the rat) during the daylight hours and falling by more than 80% soon after the onset of darkness, as serotonin is converted to melatonin.

Melatonin is a unique indole derivative. It acts both as a neurotransmitter and neurohormone. Melatonin is lipid soluble and rapidly crosses the blood brain barrier and other tissues. Once released from the pineal gland, which is highly vascularized, it enters both the general circulation and the cerebrospinal fluid (CSF). Melatonin acts on the central and peripheral nervous system as well as on peripheral endocrine target tissues. Laboratory studies have indicated that the primary effects of melatonin is on the neuroendocrine system where it has been shown to influence the activity of the hypothalamic-pituitary-gonadal-thyrold-adrenal axis. In addition, melatonin has been shown to be involved in the regulation of the activity of monoaminergic neurotransmitters such as dopamine, norepinephrine, gamma-aminobutyric acid (GABA) and serotonin as well as the opioid peptides (Ehrich and Apuzzo (1985) "The pineal gland: anatomy, physiology, and clinical significance. *Journal of Neurosurgery,* 63, 321–341 Anton-Tay (1974) "Melatonin: effects on brain function." *Advances in Biochemical Psychopharmacology,* 11, 315–324; Datta and King (1980) "Melatonin:effects on brain and behavior." *Neuroscience & Biobehavioral Reviews,* 4, 451–458; Rosenstein and Cardinall (1986) "Melatonin increases in vivo GABA accumulation in rat hypothalamus, cerebellum, cerebral cortex and pineal gland." *Brain Research,* 398, 403–406; Zisapel et al., (1982) "Inhibition of dopamine release by melatonin: regional distribution in the rat brain." *Brain Research,* 246, 161–163). At a cellular level, melatonin acts to produce antioxidants as by increasing CGMP. It also provides guanine nucleotides for DNA and partakes in DNA repair mechanisms and in maintenance of membranes and other intracellular components (Grad and Rozencwaig (1993) "The role of melatonin and serotonin in aging: update." *Psychoneuroendocrinology,* 18, 283–295.

In addition to the ambient light/dark cycle, the activity of the pineal gland and hence the rate of melatonin secretion is influenced also by the earth's geomagnetic field which is in the order of 30,000–60,000 nanotesia (0.3–0.6 Gauss). The earth's magnetic field is primarily a nontime-varying (DC) field with angle of incidence to the earth's surface increasing with increasing latitude. For comparison, anthropogenic magnetic fields are primarily time varying at 50 or 60 Hz and harmonic of these frequencies. Typical magnetic fields measured in residental settings range from 0.1 microtesia to 3 microtesia at 60 Hz frequency. The geomagnetic field has been a part of the environment throughout the evolution of animals and is used by certain species in their adaptive strategies. Organisms are capable of perceiving its intensity, polarity, and direction (Gould (1984) "magnetic field sensitivity in animals." *Annual Review of Physiology,* 46, 585–598). It is thought that the circadian rhythmicity of the earth's magnetic field may have an additional "Zeltgeber" (time cue) function in the organization of biological rhythms (Cremer-Bartels et al., (1984) "Magnetic field of the earth as additional zeitgeber for endogenous rhythms?" *Naturwissenschaften,* 71, 567–574; Wever (1968) "Einfluss Schwacher Elektro-magnetischer Felder auf die Circadlane Perlodik des Menschen." *Naturwissenschaften,* 55, 29–32; Bartsch et al., (1994) "Seasonality of pineal melatonin production in the rat: possible synchronization by the geomagnetic field." *Chronobiology International,* 11, 21–26).

Since the activity of the pineal gland is sensitive to the influences of the geomagnetic field it has been suggested that it functions as a magnetoreceptor as well (Semm et al., (1980) "Effects of an earth-strength magnetic field on electrical activity of pineal cells." *Nature,* 288 607–608; Semm (1983) "Neurobiological investigations on the magnetic sensitivity of the pineal gland in rodents and pigeons." *Comparative Biochemistry and Physiology,* 76A, 683–689; Olcese et al., (1988) "Geomagnetic field detection in rodents." *Life Sciences,* 42, 605–613; Demaine and Semm (1985) "The avian pineal gland as an independent magnetic sensor." *Neuroscience Letters,* 62, 119–122; Rudolph et al., (1988) "Static magnetic fields decrease nocturnal pineal cAMP in the rat." *Brain Research,* 446, 159–160). Based on histological studies and electrophysiological single unit recordings from the pineal gland of rodents and pigeons, it has been estimated that 20%–30% of pineal cells respond to magnetic field Stimulation (Semm (1983) "Neurobiological investigations on the magnetic sensitivity of the pineal gland in rodents and pigeons." *Comparative Biochemistry and Physiology.* 76A, 683–689). Electrophysiological studies by Reuss et al., (1983) "Different types of magnetically sensitive cells in the rat pineal gland" *Neuroscience Letters,* 40 23–26) have demonstrated the presence of different types of magnetically sensitive cells in the pineal gland of the rat.

Furthermore, short-term exposure of experimental animals to DC external magnetic fields of various intensities and frequencies has been shown to inhibit temporarily the secretion of melatonin while more chronic exposure may even induce ultrastructural morphological changes in the pineal gland (Bardasano et al., (1985) "Ultrastructure of the pineal cells of the homing pigeon *Columba livia* and magnetic fields (first trials)." *Journal Fuer Hirnforschung,* 26, 471–475; Semm et al., (1980) "Effects of an earth-strength magnetic field on electrical activity of pineal cells. *Nature,* 288 607–608; Welker et al., (1983) "Effects of an artificial magnetic field on serotonin N-acetyltransferase activity and melatonin content of the rat pineal gland." *Experimental Brain Research* 50, 426–432; Wilson et al., (1981) "Neuroendocrine mediated effects of electromagnetic field exposure:possible role of the pineal gland." *Life Sciences,* 45, 1319–1332; Reiter (1993) "Static and extremely low frequency electromagnetic fields exposure: reported effects on the circadian production of melatonin." *Journal of Cellular Biochemistry,* 51, 394–403). Exposure of animals to magnetic fields also has resulted in increased pineal and cerebral serotonin levels (Reiter and Richardson (1992) "Magnetic fields effects on pineal indoleamine metabolism and possible biological consequences." *FASEB Journal,* 6, 2283–2287).

The human pineal gland, likewise, is believed to be sensitive to changes in the environmental magnetic fields. Howard et al., (1965) "Psychiatric ward behaviour and geophysical parameters." *Nature,* 205, 1050–1052) made the seminal observation of a relationship between increased geomagnetic activity and the rate of admission of patients to psychiatric facilities. Rajaram and Mitra (1981) "Correlation between convulsive seizure and geomagnetic activity." *Neuroscience Letters,* 24, 187–191) and Venkatraman (1976) "Epilepsy and solar activity. An hypothesis." *Neurology* (India), 24, 1–5) reported an association between changes in the geomagnetic field due to magnetic storms and frequency of seizures in epileptic patients. Semm (1992) "Pineal function in mammals and birds is altered by earth-strength magnetic fields." In Moore-Ede, Campbell, and Relter (Eds.), *Electromagnetic Fields and Circadian Rhythmicity,* (pp. 53–62), Boston: Birhauser) observed in normal subjects placed in the center of a Helmholtz coil system that inversion of the horizontal component of the ambient magnetic field for 30 minutes at midnight resulted in a significant (70%) depression of plasma melatonin concentrations.

Melatonin is a "master hormone" involved in the regulation of a host of biological functions related to the control of neuroendocrine functions, immunomodulation, analgesia, motor behavior, mood, sleep, cognition, and neurotransmitter synthesis and release including serotonin synthesis (Datta and King (1980) Melatonin: effects on brain and behavior." *Neuroscience & Biobehavioral Reviews,* 4, 451–458; Ehrlich and Apuzzo (1985) "The Pineal Gland: anatomy, physiology, and clinical significance" *Journal of Neurosurgery,* 63, 321–341; Frazer and Brown (1987) "Melatonin: a link between the environment and behavior." *Integrative Psychiatry,* 5, 3–26; Bradbury et al., (1985) "Melatonin action in the midbrain can regulate forebrain dopamine function both behaviourally and biochemically." "In Brown and Wainwright (Eds.), *The Pineal Gland: Endocrine Aspects* (pp. 327–332) New York: Pergamon Press; Aldegunde et al., (1985) "Effects of pinealectomy on regional brain serotonin metabolism." *International Journal of Neuroscience,* 26, 9–13; Miguez et al., (1991) "Differential effects of pinealectomy on amygdala and hippocampus serotonin metabolism". *Journal of Pineal Research,* 10, 100–103; Miguez et al., (1991) "Long-term pinealectomy alters hypothalamic serotonin metabolism in the rat." *Journal of Pineal Research* 11, 75–79; Miguez et al., (1996) "Changes in serotonin level and turnover in discrete hypothalamic nuclei after pinealectomy and melatonin administration to rats." *Neurochemistry International,* 29, 651–658). Consequently, it is believed that intermittent transcranial applications of AC pulsed magnetic fields of extremely low intensity may be used therapeutically by boosting the activity of the pineal gland with resultant increased melatonin and serotonin production.

I and others working in this area believe that AC pulsed applications of magnetic fields in the picotesia range intensity administered transcranially are beneficial in the treatment of several neurological and mental disorders including epilepsy, Parkinson's disease, juvenile Parkinsonism, Alzhelmer's disease, dystonia, tardive dyskinesia, Tourette's syndrome, migraine, and multiple sclerosis (Anninos et. al., (1991) "Magnetic stimulation in the treatment of partial seizures." *International Journal of Neuroscience,* 60, 141–171; Sandyk and Anninos (1992) "Attenuation of epilepsy with application of external magnetic fields: a case report."*International Journal of Neuroscience,* 66, 75–85; Sandyk (1992) "The influence of the pineal gland on migraine and cluster headaches and the effects of treatment with picotesia magnetic fields." *International Journal of Neuroscience,* 67, 145–171; Sandyk (1992) "Weak magnetic fields as a novel therapeutic modality in Parkinson's disease." *International Journal of Neuroscience,* 66, 1–15; Sandyk (1992) "Successful treatment of multiple sclerosis with magnetic fields." *International Journal of Neuroscience,* 66, 237–250; Sandyk and Iacono (1993) "Resolution of longstanding symptoms of multiple sclerosis by application of picotesia range magnetic fields." *International Journal of Neuroscience,* 70, 255–269; Sandyk and Iacono (1993) "Reversal of visual neglect in Parkinson's disease by treatment with picotesia range magnetic fields." *International Journal of Neuroscience,* 73, 93–107); Sandyk (1994) "Alzheimer's disease: Improvement of visual memory and visuoconstructive performance by treatment with picotesia range magnetic fields." *International Journal* of Neuroscience, 76, 185–225; Sandyk (1994) "A drug naive Parkinsonian patient succesfully treated with electromagnetic fields." International Journal of Neuroscience, 79, 99–110; Sandyk (1995) "Improvement of right hemispheric function in a child with Gilles de la Tourette's syndrome by weak electromagnetic fields." International Journal of Neuroscience, 81, 199–213. Sandyk (1994) "Reversal of visuospatial hemi-inattention in patients with chonic progressive multiple sclerosis by treatment with weak magnetic fields" International Journal of Neuroscience, 79, 169–184; Sandyk (1995) "Long term beneficial effects of weak electromagnetic fields in multiple sclerosis." International Journal of Neuroscience, 83, 45–57; Sandyk (1996) "Treatment with electromagnetic fields alters the clinical course of chronic progressive multiple sclerosis, a case report." International Journal of Neuroscience, 88, 75–82; Sandyk (1996) "Freezing of gait in Parkinson's disease is improved by treatment with weak electromagnetic fields." International Journal of Neuroscience, 85, 111–124; Sandyk (1997) "Progressive cognitive improvement in multiple sclerosis from treatment with electromagnetic fields." International Journal of Neuroscience, 89, 39–51).

However, I believe that the therapeutic efficacy of externally applied magnetic fields, administered as described in the prior art, without the use of the composition, is limited by several factors:

First, the pineal gland tends to undergo calcification with progression of age and particularly in association with various systemic and neurological disorders (Trentini et al., (1987) "Pineal calcification in different physiopathological conditions in humans," in Trentini et al., Fundamentals and clinics in Pineal research, (pp. 291–304), New York: Raven Press, Welsh (1985) "Pineal calcification: Structural and functional aspects." Pineal Research Reviews, 3 41–68; Zimmerman and Bilaniuk (1982) "Age-related incidence of Pineal calcification detected by computed tomography." Neuroradiology 142, 659–662; Sandyk et al., (1990) Pineal gland calcification and tardive dyskinesia" Lancet. 335, 1528; Sandyk et al., (1991) "pineal calcification and anticonvulsont responsiveness to artificial magnetic stimulation in epileptic patients." For instance, in the case of epileptic patients it has been found that patients who demonstrated calcification of the pineal gland on computed tomography (CT) scan responded less favourably to magnetic treatment in terms of seizure control than those subjects who showed no calcification of the pineal gland (Sandyk et al., (1991) "Pineal calcification and anticonvulsant responsiveness to artificial magnetic stimulation in epileptic patients." International Journal of Neuroscience, 60, 173–175).

Second, the secretory activity of the pineal gland, as reflected by nocturnal melatonin plasma levels, diminishes with age. In addition, aging is associated with diminished capacity of the pineal gland to initiate the production of melatonin after sunset (Nair et al., (1986) "Plasma melatonin—an index of brain aging in humans?" Biological Psychiatry, 21, 141–150; Sack et al., (1986) "Human melatonin production decreases with age," Journal of Pineal Research, 3, 379–388). The decline in the secretory activity of the pineal gland with aging reflects in part the limited regenerative abilities of the pineal cells due to their neuronal derivation.

Finally, melatonin secretion is significantly decreased or its circadian rhythmicity is disrupted in various neurological and mental disorders inducing multiple sclerosis, Parkinson's disease, juvenile Parkinsonism, progressive supranuclear palsy, Shy-Drager syndrome, Alzheimer's disease, motor neuron disease, ischemic stroke, traumotric spinal cord injuries, Korsakoff's dementia, depression, eating disorders, alcoholism, obsessive compulsive disorder, trichotillomania, posttraumatic stress disorder, impulsive and aggressive behavior, chronic insomnia, sleep paralysis, builmia, and schizophrenia (Martin et al., (1984) "Decreased 6-hydroxymelatonin excretion in Korsakoff's psychosis." Neurology, 34, 966–968; Skene et al., (1990) "Daily variation in the concentration of melatonin and 5-methoxytryptophol in the human pineal gland: effect of age and Alzhelmer's disease." Brain Research, 528, 170–174; Nair et al., (1986) "Plasma melatonin rhythm in normal aging and Alzheimer's disease." Journal of Neural Transmission, 21 (suppl), 494; Sandyk and Awerbuch (1992) "Nocturnal melatonin secretion in multiple sclerosis patients with affective disorders," International Journal of Neuroscience, 68, 227–240; Miles and Philbrick (1988) "Melatonin and psychiatry." Biological Psychiatry, 23, 405–425; Fertl et al., (1993) "Circadian secretion pattern of melatonin in de novo Parkinsonian patients: evidence for phase-shifting properties of l-dopa." Journal of Neural Transmission {P-D Sect}, 5, 227–234; Ehrlich and Apuzzo (1985) "The pineal gland: anatomy, physiology, and clinical significance." Journal of Neurosurgery, 63, 321–341; Pang et al., (1990) "Acute cerebral hemorrhage changes the nocturnal surge of plasma melatonin in humans." Journal of Pineal Research, 9, 193–208; Li et al., (1989) "Rhythms of serum melatonin in patients with spinal lesions at the cervical, thoracic or lumbar region." Clinical Endocrinology 30, 47–56; Vaughan et al., (1979) "Melatonin, pituitary function and stress in humans." Psychoneuroendocrinology, 4, 351–362; Tetsuo et al., (1981) "Urinary b-hydroxy melatonin excretion in patients with orthostatic hypotension." Journal of Clinical Endocrinology and Metabolism, 53, 607–610).

In addition, several of the biological effects of melatonin are enhanced by serotonin neurons indicating that serotonin is an important mediator of the melatonin's biological signal (Olcese (1985) "Enhancement of melatonin's antigonadal action by daily injection of the serotonin uptake inhibitor fluoxetine in male hamsters." Journal of Neural Transmission, 64, 151–161; Miguez et al. (1996) "Changes in serotonin level and turnover in discrete hypothalamic nuclei after pinealectomy and melatonin administration to rats." Neurochemistry International, 29, 651–658).

It is believed that reduction in the activity of the pineal gland in these neurological and mental disorders may be related to various factors including, among others, decrease in pineal receptor sensitivity and/or density, decline in the availability of nutritional co-factors for serotonin and subsequent melatonin synthesis, decline in the capacity of pineal cells to synthesize serotonin from tryptophan, decrease sympathetic nervous system activity which provides a stimulus for melatonin synthesis, and progressive loss of neurons in the suprachlasmatic nucleus of the hypothalamus which activate the pineal gland.

Thus, a definite need exists in therapy today for an effective treatment for patients with neurological and mental disorders which are associated with and/or related pathogenetically to deficient serotonin neurotransmission and impaired pineal melatonin functions.

SUMMARY OF THE INVENTION

The present invention comprises a composition useful for treating neurological and mental disorders which are associated with and/or related pathogenetically to deficient serotonin neurotransmission and impaired pineal melatonin functions in humans the composition being administered in combination with the application of a sufficient amount of an alternating current (AC) pulsed magnetic field to the brain of a human in need of such treatment which composition comprises an effective amount of a composition which increases serotonin transmission to the human to be treated. The present invention also includes a method of treating neurological and mental disorders which are associated with and/or related pathogenetically to deficient serotonin transmission and impaired pineal melatonin functions in humans which comprises administering to a human in need thereof an effective amount of a composition which increases serotonin transmission to the human to be treated followed by the application to the brain of the human of a sufficient amount of an AC pulsed magnetic field of proper intensity, frequency, and wave characteristics (i.e., waveform, wave symmetry, and phase shift of the wave).

The present invention thus represents a substantial advance in the treatment of such medical conditions as multiple sclerosis, Parkinson's disease, Juvenile Parkinsonism, progressive supranuclear palsy (PSP), Huntington's chorea, AIDS dementia, Shy-Drager syndrome, motor neuron disease, essential tremor, autism, traumatic spinal cord injuries, ischemic stroke, diabetic neuropathy, macular degeneration, alcohol and substance abuse, trichotillomania, posttraumatic stress disorder, impulsive and aggressive behavior, chronic insomnia, sleep paralysis, bulimia, dystonia, tardive dyskinesia, epilepsy, migraine, Alzheimer's disease, depression, schizophrenia, Tourette's syndrome, Attention Deficit-Hyperactivity Disorder, anxiety and panic disorder, narcolepsy-catoplexy, obsessive compulsive disorder, akathisia and Restless-legs syndrome, myocionus, chronic pain syndromes.

The administration of the composition prior to application of the AC pulsed magnetic field is designed to increase serotonin neurotransmission as well as sensitize the pineal gland to a periodic exposure of AC pulsed magnetic fields.

Thus, while AC pulsed magnetic stimulation has been used therapeutically in the past, it has been observed in practice that when the composition of the present invention is administered prior to the application of the AC pulsed magnetic field, the patient's clinical response to the pulsed magnetic stimulation is markedly improved and the effect is sustained for a longer period of time.

According to one embodiment of the present invention, the AC pulsed magnetic field is applied in two applications, an initial application is applied to the brain of the patient followed by an interval of time and then a second AC pulse is applied.

When treating patients with Parkinson's disease I have achieved best results in terms of alleviation of tremor, bradykinesia (slowness of movement) and muscular rigidity by simultaneously applying an AC pulsed magnetic field and a DC magnetic field. Preferably, both AC and DC components are applied and, following an interval of time, a second application comprising both components is applied. For patients with juvenile Parkinsonism, it is preferred that the AC pulsed frequency is 5 Hz–8.5 Hz and that in both applications the waveform be square. When treating patients with multiple sclerosis I have achieved additional benefit in terms of amelioration of fatigue, visual disturbances difficulties with gait and balance, bladder disturbances and reduction of spasticity by using modulation of the AC pulsed wave's amplitude and frequency (range of amplitude modulation: 25%–100%; range of frequency modulation: 10%–50%). Furthermore, a subset of multiple sclerosis patients experiences additional benefit by modifying the symmetry of the wave, and/or by combining the AC pulsed magnetic field with random noise of low frequency (range of frequency: 0–40 Hz), and/or by combining the AC pulsed magnetic field with a DC magnetic field, and/or by administering a two-phase AC pulsed sinusoidal wave with a phase shift ranging from 0° to 180°. While patients with multiple sclerosis derive therapeutic benefit when the AC pulsed magnetic field is applied over the head through a helmet-like transducer, some patients, particularly women, report greater benefit when the AC pulsed magnetic fields are applied over the temples through a transducer embedded in an earphone-like headset. In these patients the magnetic fields are applied either simultaneously over both temples, or alternating from side- to-side (i.e., right to left) at an interval of 5–30 second Moreover, this group of patients usually experiences benefit when the amplitude (i.e., strength) of the AC pulsed magnetic field is higher then the amplitude employed through the helmet-like transducer (i.e., 7.5–75 picotesia flux density) reaching a strength of up to 1 microtesia flux density. In patients with Gilles de la Tourette's syndrome, I have achieved best results when the AC pulsed magnetic field is combined with a low frequency random noise (0–40 Hz).

According to a preferred embodiment of the present invention, the composition which is administered prior to the application of the AC pulsed magnetic field, comprises an effective amount of a serotonin precursor, an effective amount of a stimulant to increase plasma tryptophan concentrations, a sufficient amount of a stimulant to facilitate the transport of tryptophan into the brain of the human, an effective amount of a stimulant of serotonin synthesis, an effective amount of a serotonin reuptake inhibitor, an effective amount of a stimulant of serotonin release and an effective amount of a stimulant of serotonin receptors. Particularly good results are obtained by additionally increasing brain serotonin concentrations. I achieve this by having my patients increase their intake of the amino-acid tryptophan in their diet 4–8 weeks prior to the application of the magnetic field by consuming foods that are rich in tryptophan such as turkey (preferably 4 ounces twice a week), milk (preferably 8 ounces per day of whole, low fat, or skim), bananas (preferably 1 per day), nuts (preferably 1–2 ounces per day), and dry-roasted sunflower seeds (preferably 3–4 ounces per day). This nutritional regimen is recommended particularly for patients with multiple sclerosis, depression, obsessive compulsive disorder, anxiety and panic disorder, Giles de la Tourette's syndrome, Alzheimer's disease, motor neuron disease, autism, alcohol abuse, trichotillomania, posttraumatic stress disorder, and for the management of pain syndromes.

According to a further embodiment of the present invention, the serotonin precursor is L-tryptophan (L-TP) or L-5-hydroxytryptophan (L-5-HTP). L-TP or L-5-HTP may be combined with co-factors for serotonin synthesis such as vitamin $B_1$ (thiamine), vitamin $B_3$ (nicotinic acid), vitamin $B_6$ (pyridoxine) and vitamin C (ascorbic acid) as well as folic acid, biotin, S-adenosylmethionine, and vitamin D. Since serotonin present in the bloodstream is excluded by the blood-brain barrier from entry into the brain, the administration of precursors such as L-TP or L-5-HTP is used to increase brain concentrations of serotonin (Wurtman and Fernstrom (1975) "Control of brain monoamine synthesis by diet and plasma amino acids." *The American Journal of Clinical Nutrition,* 28, 638–647).

According to an embodiment of the present invention, the stimulant to increase plasma tryptophan concentrations is a solicylate. L-tryptophan is usually transported in the blood in a bound or complexed form with the protein albumin, a plasma component. It has been shown that various salicylates displace tryptophan from its protein binding site with albumin in blood plasma thereby raising the free or unbound tryptophan concentration in the blood. The bond-breaking effect exerted by salicylates on the binding of tryptophan to albumin causes a greater availability of free tryptophan molecules for diffusion into the brain (Tagliamonte et al., (1973) "Increase of brain tryptophan and stimulation of serotonin synthesis by salicylate." *Journal of Neurochemistry*, 20, 909–912). While aspirin is the salicylate preferred, any other pharmaceutically acceptable salicylate such as sodium salicylate would serve as well.

According to a further embodiment of the present invention, the stimulant to facilitate the transport of tryptophan into the brain is preferably vitamin $B_3$, chromium (preferably chromium picolinate) or a mixture thereof. Chromium is an essential co-factor to insulin production and action (Rabinowitz et al., (1983) "Effects of chromium and yeast supplements on carbohydrate and lipid metabolism in diabetic men." *Diabetes Care*, 6, 319–327). Insulin, in turn, facilitates the entry of tryptophan into the brain by inhibiting the uptake of the branched chain amino-acids leucine, isoleucine, and valine which compete with tryptophon for entry into the brain (Wurtman and Fernstrom (1976) "Control of brain neurotransmitter synthesis by precursor availability and nutritional state." *Biochemical Pharmacology*, 25, 1691–1696).

According to a further embodiment of the present invention, the stimulant of serotonin synthesis is preferably vitamin B1, vitamin B3, vitamin B6, blotin, S-adenosyimethionine, vitamin D, folic acid, ascorbic acid, magnesium or mixtures of two or more thereof.

According to a further embodiment of the present invention, the serotonin reuptake inhibitor is sertraline, nefazodone, trazodone, fluoxetine or a mixture thereof. According to a further embodiment of the present invention, the stimulant of serotonin release is preferably fenfluramine (Fuller (1986) "Pharmacologic modification of serotonergic functions: drugs for the study and treatment of psychiatric and other disorders." *Journal of Clinical Psychiatry*, 47 (suppl 4), 4–8).

According to a further embodiment of the present invention, the stimulant of serotonin receptors is preferably ergoloid mesylates (Hydergine®), pergolide mesylate or buspirone. Hydergine® has been shown to improve mental alertness and memory functions in normal subjects and those with organic mental deterioration an effect which is related partly to its stimulating properties of serotonin receptors in the brainstem reticular formation (Depoortere et al., (1975) "Neuropharmacological studies on Hydergine." *Triangle*, 14, 73–79. Ergot derivatives stimulate central dopamine receptors and are employed for the treatment of Parkinson's disease. However, these agents also exhibit serotonin receptor stimulating properties (Markstein (1981) "Neurochemical effects of some ergot derivatives: a basis for their antiparkinson actions." *Journal of Neural Transmission*, 51, 39–59). Buspirone (Buspar®) is a nonbenzodiazepine anxiolytic agent which acts as an agonist at the serotonin (5-HT)$_{1A}$ receptor sites. It behaves as a full agonist at the cell-body autoreceptor and as a partial agonist at postsynaptic 5-HT$_{1A}$ receptor sites (Cowen (1991) "Serotonin receptor subtypes: implications for psychopharmacology." *British Journal of Psychiatry*, 159 (suppl 12). 7–14); Eison and Temple (1986) "Buspirone: review of its pharmacology and current perspectives on its mechanism of action." *The American Journal of Medicine*, 80 (suppl 3B), 1–9).

It is preferred that the strength of the AC pulsed magnetic field, when applied over the vertex of the head through a helmet-like transducer, be in the range of 7.5 to 75 picotesia flux density (i.e., $7.5 \times 10_{-12}$ to $75 \times 10_{-12}$ tesia flux density). It is preferred that the strength of the AC pulsed magnetic field, when applied over the temples through a transducer embedded in an earphone-like headset, be in the range of 7.5 picotesia to 1 microtesia flux density (i.e., $7.5 \times 10_{-12}$ to $1 \times 10_{-6}$ tesia flux density). It has been found most beneficial that the duration of the first AC pulse be 15–20 minutes. The magnetic field is a time varying field with a waveform which is sinusoidal, triangular, trapezoidal, square, or sawtooth or a composite thereof, dependent upon the condition to be treated.

It is particularly preferred that the two AC magnetic field pulses be applied following administration of the composition of the present invention. It is preferred that the duration of the first AC pulse be in the range of 15–20 minutes and the duration of the second AC pulse be in the range of 15–45 minutes. The AC frequency and waveform of each pulse will vary with the condition to be treated. In the case of multiple sclerosis, the AC frequency should be 2 Hz–5 Hz with the waveform being sinusoidal, trapezoidal, square, or sawtooth. The amplitude of the pulsed magnetic field wave may be modulated at a range of 25%–100% and the frequency of the wave at a range of 10%–50%, in addition, the symmetry of the wave may be varied, and/or a DC field is combined with the AC pulsed magnetic field, and/or the magnetic field is applied over the temples in the form of a two-phase AC pulsed sinusoidal wave with a phase shift ranging from 0° to 180°, and/or a low frequency random noise (0–40 Hz) is applied in combination with the AC pulsed magnetic field. The AC frequency for the treatment of Parkinson's disease, juvenile Parkinsonism, progressive supranuclear palsy, essential tremor, Huntington's chorea, AIDS dementia, Shy-Drager syndrome, motor neuron disease, diabetic neuropathy, ischemic stroke, macular degeneration, Alzheimer's disease, migraine, dystonia, myoclonus, Restless-legs syndrome and akathisia, narcolepsy, Tourette's syndrome, tardive dyskinesia, depression, anxiety and panic disorder, alcohol abuse, trichotillomania, posttraumatic stress disorder, impulsive and aggressive behavior, chronic insomnia, bulimia, obsessive compulsive disorder, Attention deficit and hyperactivity, pain syndromes, and schizophrenia is preferably 5 Hz or above. For the treatment of seizure disorders, it is preferred that the AC frequency of the first pulse be in the range of 4 Hz–5 Hz and the frequency for the second AC pulse be in the range of 5 Hz–7 Hz. For the treatment of autism and traumatic spinal cord injuries, it is preferred that the AC frequency of the first pulse be in the range of 3 H–5 Hz and the frequency for the second AC pulse be in the range of 4 Hz–7 Hz.

It is preferred that the patient's eyes be shielded during the application of the AC pulsed magnetic field.

It has also been found to be most effective when the treatment of the present invention begins 4–8 weeks, particularly 6–8 weeks, prior to the application of the pulse by administration of the elements of the composition of the present invention.

For the treatment of juvenile Parkinsonism, the preferred AC pulsed frequency is 5 Hz–8.5 Hz.

For the treatment of progressive supranuclear palsy, the preferred AC pulsed frequency is 5 Hz–8 Hz.

For the treatment of motor neuron disease, the preferred AC pulsed frequency is 5 Hz–8 Hz.

For the treatment of essential tremor, the preferred AC pulsed frequency is 5 Hz–8 Hz.

For the treatment of Huntington's chorea, the preferred AC pulsed frequency is 5 Hz–8 Hz.

For the treatment of AIDS dementia, the preferred AC pulsed frequency is 5 Hz–8 Hz.

For the treatment of Shy-Drager syndrome, the preferred AC pulsed frequency is 5 Hz–8 Hz.

For the treatment of traumatic spinal cord injuries, the preferred AC pulsed frequency is 3 Hz–7 Hz.

For the treatment of ischemic stroke, the preferred AC pulsed frequency is 5 Hz–8 Hz.

For the treatment of autism, the preferred AC pulsed frequency is 3 Hz–7 Hz.

For the treatment of macular degeneration, the preferred AC pulsed frequency is 5 Hz–7 Hz.

For the treatment of diabetic neuropathy, the preferred AC pulsed frequency is 5 Hz–7 Hz.

For the treatment of alcohol and substance abuse, the preferred AC pulsed frequency is 5 Hz–7 Hz.

For the treatment of trichotillomania, the preferred AC pulsed frequency is 5 Hz–7 Hz.

For the treatment of posttraumatic stress disorder, the preferred AC pulsed frequency is 5 Hz–8 Hz.

For the treatment of impulsive and aggressive behavior, the preferred AC pulsed frequency is 5 Hz–8 Hz.

For the treatment of chronic insomnia, the preferred AC pulsed frequency is 5 Hz–8 Hz.

For the treatment of sleep paralysis, the preferred AC pulsed frequency is 5 Hz–7 Hz.

For the treatment of bulimia, the preferred AC pulsed frequency is 5 Hz–8 Hz.

It is preferred that the AC pulsed magnetic fields are conveniently applied to the patient's head using a helmet-like transducer array. Alternatively, the fields are applied over the temples through a transducer embedded in a earphone-like headset. The helmet-like transducer array preferably comprises an array of coils comprising four rows of four coils. Alternatively, the helmet-like transducer array may comprise an array of coils comprising four rows of six coils. Preferably, the helmet-like transducer array comprises an array of coils which are flat i.e. two dimensional or helical i.e. three dimensional. The transducer embedded in a earphone-like headset comprises three solenoid-like coils which are connected in parallel.

BRIEF DESCRIPTION OF THE DRAWINGS

FIGS. 1A–C show test results of a patient afflicted with Parkinson's disease treated with an AC pulsed magnetic field without the prior administration of the composition of the present invention. The test is a sequence of drawing assignments, in this case the drawing of a bicycle, wherein FIG. 1A shows the results of the drawing test prior to the application of magnetic treatment, FIG. 1B shows the results of the drawing obtained five minutes after a single AC pulsed magnetic treatment, and FIG. 1C shows the drawing results obtained following 30 minutes of magnetic treatment wherein a second AC pulse has been administered after a 15 minutes interval;

FIGS. 2A–C show attempts at drawing by a patient afflicted with Alzheimer's disease wherein FIG. 2A shows an attempted drawing of a house prior to magnetic treatment, FIG. 2B shows an attempted drawing of the house by the patient after two fifteen minute AC pulses of magnetic treatment, and FIG. 2C shows a drawing produced by the patient after treatment with the composition followed by administration of two fifteen minute AC pulses of magnetic fields;

FIGS. 3A–D show the drawings by a patient afflicted with schizophrenia wherein FIG. 3A show the patient's drawing of a house prior to magnetic treatment, FIG. 3B shows the patient's drawing of a house after administration of a placebo magnetic treatment, FIG. 3C shows an attempt by the patient to draw the house after a treatment of two AC magnetic pulses, FIG. 3D shows the patient's drawing (on a reduced scale) after treatment according to the present invention;

FIGS. 4A–C show attempts at a drawing by a 6½ year old child afflicted with Gilles de la Tourette's syndrome wherein FIG. 4A shows an attempted drawing of the human figure prior to magnetic treatment which showed distortions, lack of perspectives and details, and abnormal presentation of the hands each having three projections for fingers. FIG. 4B shows the child's drawing of the human figure after two fifteen minutes AC pulses of magnetic treatment, and FIG. 4C shows the child's drawing after treatment according to the present invention which comprised administration of the composition of the present invention followed by the application of two fifteen minute AC pulses of magnetic fields according to the present invention.

FIGS. 5A–C show attempts at a drawing of the Archimedes spirals by a patient afflicted with essential tremor wherein FIG. 5A shows an attempted drawing of the spirals with the right hand prior to magnetic treatment which demonstrates the tremor. Also, note the impact of tremor on the patient's signature and date of study, FIG. 5B shows an attempted drawing of the spirals following application of AC pulsed magnetic fields of 15 minutes duration employing a 5 Hz sinusoidal wave with a 50% amplitude modulation. Note reduction in the severity of the tremor and the improvement in patient's signature and date of the study. FIG. 5C shows an attempted drawing of the spirals following application of the second AC pulsed magnetic treatment of 30 minute duration employing a 7 Hz sinusoidal wave with a 50% amplitude modulation wherein the second AC pulse has been administered after a 30 minute interval according to the present invention.

FIG. 6A shows an attempted drawing of a clock, bicycle, and a house prior to magnetic treatment. Note the small size of the drawing of the bicycle and house reflecting the micrographia (small script) of Parkinsonism. FIG. 6B shows the patient's drawings after a single AC pulsed magnetic treatment of 15 minute duration employing a 5 Hz sinusoidal wave. Note the immediate increase in the size of the drawings and the presentation of a more elaborate house. FIG. 6C shows the patient's drawings after the application of a second sinusoidal AC pulsed magnetic field of 7.5 Hz frequency wherein the second pulse has been administered after a 15 minute interval according to the present invention. Note further increase in the size of the drawings and the detailed presentation of the house.

FIG. 7A demonstrates the patient's drawing of a bicycle before magnetic treatment. Note the small size of the bicycle characteristic of the Parkinsonian micrographic. In addition, note the lack of essential details in the bicycle such as the drive chain, pedals, and spokes as well as the improper position of the seat and the differences in the size of the wheels with the front wheel being twice the size of the rear wheel. FIG. 7B shows the patient's drawing of a bicycle after 40 minutes of magnetic treatment composed of two 20-minute AC pulses of magnetic fields separated by a 15-minute interval. The AC frequency of the first treatment was 5 Hz and that of the second treatment was 7.5 Hz using a square wave in both applications. Note the increase in the size of the bicycle and the inclusion of additional details such as spokes, a drive chain and pedals. FIG. 7C shows the patient's spontaneous drawing of a bicycle three months later during which time he received weekly treatments with magnetic fields which were applied in conjunction with the composition. Note the dramatic increase in the size of the bicycle indicating reversal of the Parkinsonian micrographia. In addition, note the detailed demonstration of the bicycle indicating improvement in mechanical reasoning and visuographic skills.

FIG. 8B shows the patient's attempt to recall the Figure prior to magnetic treatment demonstrating an almost 100% degradation of details reflecting poor visual memory related to right temporal lobe dysfunction. FIG. 8C shows the patient's attempt to recall the Rey Complex Figure four weeks later during which time he received twice weekly treatment with magnetic fields according to the present invention. A treatment comprised two successive applications of AC pulsed magnetic fields each of 20 minutes separated by an interval of 15 minutes. The AC pulsed frequency of the first treatment was 5 Hz and of the second treatment 7 Hz using a sinusoidal wave. Note the dramatic increase in his ability to recall the Figure indicating marked improvement in visual memory.

FIG. 9 is a schematic diagram showing connections of a signal generator to an array of coils for impressing magnetic fields upon a patient's head;

FIGS. 10 and 10A show plan views of alternate configurations of the array of coils;

FIG. 11 is a sectional view of the array of coils taken along the line 24—24 in FIG. 10;

FIG. 12 is a stylized view showing emplacement of the array of coils upon a patient's head for impressing the magnetic fields into the patient's head; and FIG. 13 is a diagram showing pulsation of the magnetic fields.

FIG. 14 is an example showing a sawtooth graph of the pulsation.

DETAILED DESCRIPTION

Figure 1A:

The treatment of the present invention has been found to be most effective when the patient is given the elements of the applicant's composition beginning 4–8 weeks, preferably 6–8 weeks, prior to the application of the AC pulsed magnetic field which is preferably in two treatments. The composition can comprise one or more of the specific components described above. Particular components can or should be omitted using sound medical judgment including patient contraindications or lack of compatibility with other medication (s) the patient is taking.

In the initial treatment phase, the patient is given a serotonin reuptake inhibitor drug to increase the brain's concentrations of serotonin. The uptake of serotonin bock into the nerve terminal inactivates the neurotransmitter after it has been released into the synaptic cleft. Therefore, serotonin reuptake inhibitors enhance serotonergic neurotransmission by increasing the synaptic concentrations of the neurotransmitter thus permitting serotonin to act for a longer period on the postsynaptic receptor. For this purpose, it is preferred to use one of the selective serotonin reuptake inhibitors (e.g., fluoxetine, fluvoxamine, clomipramine, citalopram, paroxetine, sertraline, venlafaxine, nefazodone), preferentially sertraline (Zoloft®; 25–200 mg, orally per day) taken in the morning with breakfast or nefazodone (Serzone®; 50–600 mg, orally per day).

A second serotonin transmission enhancing drug is given at nighttime. I prefer the drug trazodone (Desyrel®) (25–100 mg., orally). This drug increases serotonergic neurotransmission by inhibiting the reuptake of serotonin in the synaptic cleft and also acts as a serotonomimetic substance through its major metabolite m-chlorophenylpiperazine (m-CCP), a direct and potent postsynaptic serotonin$_{1B}$ receptor agonist.

Clinical experience has shown that administration of these serotonergic drugs for at least four weeks prior to the initiation of pulsed magnetic treatment is one of the key components of my pharmacological composition.

On the night prior to application of magnetic fields the patient is given a serotonin precursor to augment the synthesis of serotonin and melatonin. For this purpose the inventor prefers a preparation containing the essential amino-acid tryptophan (L-tryptophan, 500 mg –3 g orally) or a preparation containing L-5-hydroxytryptophan (L-5-HTP) (100–200 mg, orally) taken at bedtime. L-5-HTP produces a more pronounced elevation of brain serotonin levels and melatonin production than L-tryptophan and is therefore preferred.

One to two hours prior to application of magnetic treatment the patient is given:

(a) a preparation containing the serotonin precursor L-tryptophan (500–1000 mg.) or L-5-HTP (100–200 mg., orally). In the experience of the inventor L-5-HTP is the agent of choice;

(b) a drug which stimulates the release of serotonin from serotonergic neurons. For this purpose I prefer the drug fenfluramine hydrochloride (Pondmin® 10–50 mg, orally); and (c) a drug which stimulates serotonin receptors from the class of ergot derivatives (e.g., bromocriptine, lisuride, pergolide and mesulergine). I prefer to use the drug pergolide mesylate (Permax®, 0.025–0.05 mg., orally). Alternatively, buspirone (Buspar®, 2.5–7.5 mg., orally) can be used to stimulate serotonin receptors. These drugs are used as part of the composition exclusively in patients with multiple sclerosis.

In my experience, the administration of a serotonin precursor alone or combined with a serotonin releasing agent and an ergot derivative or buspirone (in the case of multiple sclerosis) one to two hours preceding magnetic treatment is highly important for the success of the procedure; not only is the effect of magnetic stimulation more pronounced, but the duration of the clinical response to the procedure is significantly longer when the patient receives my composition prior to application of the magnetic field.

The procedure continues with application of a pulsed AC magnetic fields at an oscillatory frequency dependent on the specific neurological or mental disease being treated. Magnetic fields are applied over the scalp or over the temples in a pulsed exposure (i.e., "on/off"). This method was chosen as several experimental studies have demonstrated that intermittent exposure to magnetic fields is biologically more effective than static or continuous wave sinusoidal exposure (Wilson et al., (1992) "Effects of electromagnetic field exposure on neuroendocrine function." In Moore-Ede et al., *Electromagnetic fields and circadian rhythmicity* (pp. 29–50), Birhauser: Boston). Magnetic treatment is applied during the day, but preferentially at nighttime (at least 2 hours after sunset) since nighttime exposure has been shown in experimental animals to induce greater melatonin response to magnetic fields than daytime exposure (Welker et al., (1983) "Effects of an artificial magnetic field on serotonin N-acetyltransferase activity and melatonin content of the rat pineal gland." *Experimental Brain Research,* 50, 426–432). Magnetic fields are applied in a quiet and magnetically unshielded room with the patient's eyes covered with eye shields to prevent exposure to light thus maximizing pineal stimulation. Magnetic fields are applied about 1–2 minutes after shielding of the patient's eyes. This period is chosen since it has been shown that melatonin secretion is increased within one minute after exposure of a subject to a dark environment. During the interval between magnetic treatments the patient may remove the eye shields.

The first magnetic pulse is given for a period of 15–20 minutes using an AC frequency of 2 Hz–5 Hz. The optimum frequency varies with the specific disease being treated. In my experience, this is the time which is usually required until one can observe that the patient's face becomes pale. After a break of 15–45 minutes, during which time the patient's facial color has returned to normal, a second magnetic pulse is applied for a period of 15–45 minutes using a higher AC frequency of 4 Hz–8.5 Hz. During this period the patient's face may become pale once again usually more intensively than after application of the first magnetic pulse. According to my experience, the application of the second AC pulse is extremely beneficial as it produces a more profound clinical effect. In addition, application of a second AC pulse is also associated with a greater degree of facial pallor. It is of note that facial pallor is usually more prominent in patients who have received my composition prior to the application of magnetic fields.

Evidence of the success of the treatment of the present invention is demonstrated by improvement in motor, sensory, and autonomic functions as well behavioral and intellectual skills, sleep, mood, and level of energy. For example, in the case of patients having multiple sclerosis including those with a chronic progressive course of the disease noticeable improvements in vision, bladder control, balance, motor coordination, sensory symptoms, lessened fatigue as well as mood, sleep, and cognitive functions have been observed. In the laboratory, there was objective documentation that this treatment of the present invention was associated with electrophysiological changes in the recordings of the visual and auditory brainstem evoked potential amplitudes and latencies.

In the case of patient having Juvenile Parkinsonism with onset of first symptoms prior to age 45, I have observed improvement in motor symptoms such as tremor, rigidity, bradykinesia, facial expression and speech as well as improvement in levodopa-related motor complications such as "on-off" dyskinesias, freezing of gait and dystonic movements. There was also improvement in the efficacy and duration of the antiparkinsonian medications and some patients were able to reduce the dosage of the medications without experiencing deterioration in symptoms. Pulsed applications of magnetic fields also resulted in improvement in autonomic functions such as excessive sweating, seborrhea, bowel constipation, sexual dysfunction, and postural hypotension. In addition, there was improvement in nonmotor symptoms such as mood, sleep, pain, and cognitive functions particularly short term memory, spatial orientation, and visuospatial functions.

In the case of a patient having progressive supranuclear palsy (PSP), I have observed improvement in motor symptoms classically associated with Parkinsonism such as rigidity, bradykinesia, shuffling gait, and loss of facial expression as well as in symptoms characteristic of the disease such as axial dystonia, postural instability, pseudobulbar palsy, ophthalmoplegia of vertical gaze, and intellectual deterioration related to frontal lobe dysfunction. In terms of motor symptoms, patients experienced improvement in balance and posture resulting in markedly diminished frequency of falling and attenuation of freezing of gait. There was generalized improvement in mobility. Facial expression became more vivid and there was consistent improvement in conjugate ocular movements, speech and handwriting with resolution of micrographia. Mentally, I have observed improvement in mood and level of energy and cognitively, there was improvement in short term memory, visual recall, and comprehension.

In the case of patients having motor neuron disease (amyotrophic lateral sclerosis, ALS), I have observed improvement in symptoms related to upper motor neuron degeneration such as difficulties with speech, swallowing, manual dexterity, and shoulder and arm strength as well as in symptoms related to lower motor neuron degeneration including weakness of the back and leg muscles, flexor spasms and cramping in the toes. There was also improvement in gait and balance. Patients reported diminished muscle twitching in the upper and lower extremities, increased endurance, and diminished fatigue.

In the case of patients having essential tremor, I have observed rapid reduction in the amplitude of tremor in the hands thus improving the patient's ability to perform writing, eating, drinking, and other activities of daily living. Improvement also occurred with respect to tremor of the head as well as the voice which causes speech distortion resulting in a fluctuating and rhythmical dysphonia.

In the case of patients having Huntington's chorea, a hereditary disorder characterized clinicaly by the presence of choreiform movements and progressive dementia usually beginning during early middle life, I have observed attenuation of the choreiform movements in the face and extremities and improvement in speech and facial expression. However, the most dramatic changes occurred in mental and cognitive functions resulting in improved mood, diminished irritability, increased social interactions, increased alertness and improved spatial orientation, short term memory, judgement and reasoning.

In the case of a patient having AIDS dementia complex, a progressive cognitive impairment which occurs in about 25% of AIDS patients, I have observed improvement in various cognitive functions such as mental concentration, alertness, short-term memory, calculation, visuospatial functions as well as improvement in emotional disturbances including mood, apathy, irritability, and anxiety. Resolution of mental confusion has been the most dramatic immediate mental change observed in a patient having AIDS dementia.

In the case of a patient having Shy-Drager syndrome, a neurological disorder characterized by autonomic failure with any combination of parkinsonism, pyramidal dysfunction, cerebellar ataxia and lower motor neuron deficits, I have observed improvement in parkinsonian features (i.e., bradykinesia, rigidity, mask-like facial expression, hypophonia) and stability of gait as well as improvement in autonomic functions such as bowel constipation, sphincter control, peripheral edema and postural hypotension resulting in diminished syncopal attacks.

In the case of a patient having traumatic spinal cord injury resulting in paraparesis and disturbances of sphincter control, I have observed improvement in motor functions with resultant increased strength and range of motion of the paralysed extremities. There was also improvement in bladder control resulting in diminished frequency and improved voiding. Likewise, in patients having hemiparesis resulting from ischemic stroke, I have observed that AC pulsed applications of magnetic fields improved muscle strength and diminished spasticity in the affected limbs. In addition, AC pulsed applications of magnetic fields had a positive impact on the patient s mood, thus facilitating a more effective physical rehabilitation.

In the case of a patient having autism, a disorder characterized by profound failure to develop social relationships, defective speech, and ritualistic or compulsive behaviors, I have observed improvement in social interactions with family members and friends, increased verbal communication, improved speech and ability to carry a conversation, increased range of interests, improved self-esteem, decreased stereotyped movements, attenuation of hyperactivity and obsessive compulsive behavior and improvement in mood and sleep. Treatment with electromagnetic fields also improved autistic symptoms in children having Gilles de la Tourette's syndrome.

In the case of a patient having age-related macular degeneration, which is the leading cause of permanent visual loss in the elderly, I have observed that AC pulsed applications of magnetic fields resulted in rapid improvement in central vision in the affected eye. As a result of this treatment vision was restored to the extent that patients were able to resume reading.

In the case of a patient having diabetic neuropathy, which is associated with symmetric and bilateral loss of vibration and temperature sensation and pain in the lower extremities, I have observed marked amelioration of pain by AC pulsed applications of magnetic fields. As a result patients were able ambulate without experiencing severe discomfort which is frequently caused by burning sensation in the legs and feet.

In the case of a patient having alcohol abuse/dependency, I have observed that AC pulsed applications of magnetic fields diminished alcohol craving and consumption.

In the case of a patient having trichotillomania, I have observed that AC pulsed applications of magnetic fields attenuated the frequency and urge to compulsively pull hair.

In the case of a patient having posttraumatic stress disorder, a disorder in which the individual reexperiences a traumatic event along with decreased responsiveness to and avoidance of current events associated with the trauma and physiologic hyperarousal which include startle reactions, intrusive thoughts, sleep disturbances, impulsivity and lack of concentration, I have observed that AC pulsed applications of magnetic fields resulted in attenuation of anxiety and startle responses, improvement in mood, reduction in intrusive thoughts, improvement in sleep, and decrease in panic reactions and impusivity.

In the case of patients exhibiting impulsive and aggressive behavior (e.g., patients with Tourette's syndrome, multiple sclerosis, organic dementia, post-traumatic brain injury), I have observed immediate and long-term attenuation or resolution of this behavior and additionally, resolution of suicidal thoughts. In the case of patients having Gilles de la Tourette's syndrome and exhibiting auto-aggressive behavior (i.e., self-mutilation), I have observed marked reduction of this behavior which often resulted in serious injuries to the patient.

In the case of a patient having chronic insomnia, I have observed that pulsed applications of magnetic fields enhanced the patient's ability to fall asleep and maintain deep sleep without nocturnal awakenings. Upon arousal patients report sleep benefit waking up fully rested and frequently recalling having vivid and pleasant dreams.

In the case of a patient having sleep paralysis, a disorder characterized by the sudden inability to perform voluntary movements at the onset of sleep or upon awakening in the morning associated with hallucinatory phenomena and dream-like states, I have observed that pulsed applications of magnetic fields gradually diminished the frequency of these episodes and over a period of several months these episodes eventually resolved.

In the case of a patient having bulimia, an eating disorder characterized by binge eating often followed by self-induced vomiting, I have observed attenuation of binge eating, improvement in mood and self-esteem, reduction in impulsivity, emotional lability and irritability and decreased carbohydrate craving.

Once the composition has been administered, the AC pulsed magnetic fields are subsequently applied via an external magnetic coil assembly, or transducer. The transducer is constructed of flexible substrate which allows the transducer to be bent and positioned on the head of a patient in the form of a helmet. The transducer is constructed of a set of coils positioned side-by-side in a two-dimensional array. In the preferred embodiment of the invention, the transducer is constructed of 16 coils arranged in a matrix of four rows by four columns, and the area of each coil is 3.14 $cm^2$. When these coils are carrying an electric current, they produce magnetic fields with lines of force parallel to the axes of the respective coils. The locations of the coils are such that the resultant magnetic fields are uniform. The produced magnetic fields are alternating and can be in the frequency range of 1 Hz to 10 KHz, and their intensity can be less than approximately 60 microtesia. For clinical purposes herein, it is preferred to employ magnetic fields strength in the range of 7.5–75 picotesia flux density with an AC frequency in the range of 2 Hz–8.5 Hz, the optimum frequency depending on the specific disease. In the experience of the inventor higher amplitudes of the exposed magnetic fields above 75 picotesia and up to 1000 picotesia do not provide additional clinical benefit. The AC pulsed magnetic fields may also be applied over the temples through a transducer embedded in an earphone-like headset. Each headset contains 3 solenoid-like coils which are connected in parallel and the area of each coil is 1 cm2. In this setting the pulsed magnetic fields are applied either simultaneously over both temples, or alternating from side-to-side (i.e., right to left) at an interval of 5–30 seconds. For clinical purposes the strength of the AC pulsed magnetic field emitted through the transducer embedded in the earphone-like headset is higher reaching an intensity of up to 1 microtesia flux density.

To maintain the effects of the treatment, "maintenance therapy" is implemented during which time the procedure may be repeated once to three times every week depending on the patient's clinical needs. During the period of "maintenance therapy" the patient continues treatment with all the elements of the composition except for those which are given the night before (i.e., L-tryptophon or L-5-HTP) and just prior to the application of magnetic treatment (L-tryptophan or L-5-HTP, fenfluramine, and pergolide mesylate). During the entire treatment period as well as the "maintenance therapy" the patient continues to receive the usual medications for the disease. For instance, in the case of Parkinson's disease the patient continues to use his antiParkinsonian medications while receiving the composition and the magnetic treatment. In some instances, antiParkinsonian medications may be reduced during the period of magnetic treatment or "maintenance therapy" based on the judgement of the doctor.

A further benefit of the present invention has been found in that the effects of the pulsed magnetic treatment may be enhanced by applying the magnetic fields in a specific AC frequency for each disease state. It is noteworthy that the clinical response to magnetic fields applied through the helmet-like transducer is not influenced significantly by the strength of the magnetic fields as long as the amplitude of stimulation is in the picotesia range. Specifically, no apparent difference in the clinical response of these patient's is noted when the strength of the magnetic fields applied ranges from 7.5 picotesia to 75 picotesia flux density (i.e., ten-fold increase in the amplitude did not impact on the clinical response). However, when magnetic fields are applied over the temples through a transducer embedded in a earphone-like headset, the strength of the field required to achieve therapeutic benefit is higher ranging from 7.5 picotesia to 1 microtesia flux density.

It has been observed that patients with chronic progressive multiple sclerosis experience the greatest degree of improvement of symptoms when administered magnetic fields of low frequency in the range of 3 Hz–5.5 Hz (optimal range 3 Hz–4.5 Hz). With higher frequencies, patients may even experience worsening of symptoms.

On the other hand, patients with Parkinson's disease usually require a higher combined AC/DC pulsed magnetic field frequency of stimulation. The best clinical response has been obtained using the range of 5 Hz–8.5 Hz. Patients with Alzheimer's disease usually require a similar range of frequencies, namely 5 Hz–8 Hz, to achieve the most favorable clinical response. Likewise, patients with dystonia, tardive dyskinesia, juvenile Parkinsonism, progressive supranuclear palsy, migraine, motor neuron disease, Huntington's chorea, AIDS dementia, Shy-Drager syndrome, essential tremor, ischemic stroke, diabetic neuropathy, macular degeneration, depression, anxiety and panic disorder, obsessive compulsive disorder, trichotillomania, posttraumatic stress disorder, chronic insomnia, sleep paralysis, bulimia, and schizophrenia require a frequency of stimulation in the range of 5 Hz–8.5 Hz.

In summary, therefore, it appears that the AC frequency of the applied magnetic fields is more critical to the clinical response to magnetic treatment than the intensity of the magnetic fields. It is possible that the pineal gland is differently affected in these neurological and mental disorders requiring a different AC pulsed frequency of stimulation to be activated in each of these disorders.

With reference to FIGS. 9–12, there is shown a transducer 30 which is employed in the practice of the invention to impress magnetic fields upon the brain of a patient. The transducer 30 comprises a set of coils 32, and is placed on the head of a patient 34. Upon energization of the coils 32 with electric current, the coils 32 produce magnetic fields which are directed into the brain, and particularly into the areas of the pineal gland, of the patient 34. The patient 34 holds a cup 36 to demonstrate the inventive feature of ingesting various pharmacological and nutritional components of the composition prior to application of the magnetic fields. Electric current is applied to the coils 32 by a driver 38, the driver 38 including a voltage generator 40 and an output resistor 42 by which the generator 40 is coupled to the coils 32. Also included in the driver 38 is a timer 44 for activating the generator 40 to provide a sequence of pulses of output voltage which are applied to the resistor 42. The resistor 42 has a resistance of approximately 0.5 megohm in the preferred embodiment of the invention, and the coils 32 are connected in series to provide a total resistance of approximately one ohm between the terminals 46 and 48 of the transducer 30. A volt meter 50 is connected between output terminals 52 and 54 of the generator 40 to provide an indication of the magnitude of the output voltage of the generator 40.

The coils 32 and the resistor 42 constitute a series circuit between the terminals 52 and 54 of the generator 40. Since the internal impedance of the driver 38, as provided by the resistor 42, is several orders of magnitude greater than that of the transducer 30, the voltage generator 40 in combination with the resistor 42 acts as a current source to provide a current to the transducer 30 proportional to the voltage outputted by the generator 40. In view of the current-source function of the driver 38, the meter 50 also provides an indication of the magnitude of the current flow in the coils 32 of the transducer 30. The intensity of the magnetic fields produced by the current in the coils 32 is proportional to the magnitude of the current and, accordingly, the reading of the meter 50 serves also as an indication of the intensity of the magnetic fields applied by the transducer 30 to the patient 34. The generator 40 is of well-known construction and provides a voltage with a periodic waveform. The generator 40 includes controls for selecting the AC frequency of the voltage, the waveform of the voltage, and the amplitude of the voltage. By way of example, the voltage may be a steady DC voltage, or may be varied in frequency over a range of 0.1 Hz to 10,000 Hz. The waveform may be sinusoidal, triangular, trapezoidal, square, sawtooth, or a combination of more than one of these waveforms such as the sum of square plus sinusoid as shown in FIG. 13, by way of example.

The transducer 30 comprises a substrate 56 which supports the coils 32 in their respective positions in a two-dimensional array 58. By way of example in the practice of the invention, in one embodiment of transducer 30, the array 58 has a total of 16 of the coils 32 arranged in four rows, each of the rows having four of the coils 32, as shown in FIG. 11. Each coil 32 has, typically four or five turns, and has a diameter of approximately two centimeters, with an area of approximately three square centimeters. In a second embodiment of the transducer 30A, there is array 58A of the coils 32A having a total of 24 coils arranged in four rows each having six coils 32A, as shown in FIG. 10A. A cover layer 60 is disposed on top of the substrate 56 and the coils 32. The substrate 56 and the cover layer 60 are formed of a flexible electrically-insulating plastic material which permits flexing of the transducer 30 to conform to the curvature of the patient's head. The coils 32 are formed of a flexible electrically-conductive material such as copper which permits the foregoing flexing of the transducer 30.

In the case of energization of the coils 32 with a sinusoidal current, the generator 40 is operated to output a peak voltage, typically, of four volts relative to ground. This voltage provides a peak current of eight microamperes which is more than enough current to provide a peak magnetic field intensity of 60 picotesia. The output voltage of the generator 40 is adjusted to provide a desired intensity to the resultant alternating magnetic fields. If desired, the resistance of the resistor 42 may be reduced to provide still larger values of current for greater intensity of magnetic fields. Upon energization of the coils 32 with electric current, the resultant magnetic fields have lines of force parallel to the axes 62 of the respective coils 32. The locations of the coils 32 provide that the resultant magnetic fields are uniform. The driver 38 and the transducer 30 or 30A are capable of providing alternating magnetic fields in a frequency range of 0.1 Hz to 10 KHz, and strength up to 60 microtesia. Typically, in the practice of the invention, the strength of the alternating magnetic fields is in the range of 7.5–75 picotesia flux density, and the frequency is in the range of 2 Hz–8.5 Hz However, when the magnetic fields are applied over the temples through a transducer embedded in an earphone-like headset, the strength of the AC pulsed magnetic field is higher ranging from 7.5 picotesia to 1 microtesia flux density.

FIG. 13 shows a sequence of two pulses of magnetic fields wherein the direction and amplitude of the magnetic fields alternate in sinusoidal fashion. The sinusoidal form of the alternating magnetic fields is employed in the preferred embodiment of the invention. However, it is understood that some other waveform such as the aformentioned triangular trapezoidal or square or sawtooth waveform may be used if desired (FIG. 14). For example, in the case of the trapezoidal waveform, the rise and the fall times of the waveform together may occupy from 20% to 40% of each period of the waveform. Within each pulse, the AC frequency is held constant in the preferred embodiment of the invention. However, if desired, the AC frequency may be altered, as by a frequency ramp wherein the frequency increases during the pulse, such that the end frequency is greater than the initial frequency by 10%–30%.

FIG. 13 also shows the duration, A, of the first AC pulse, and the duration, B, of a rest interval or break between the AC pulses, and the duration, C, of the second AC pulse. The first AC pulse has a duration, A, of 15–20 minutes, the break, B, is in the range of 15–45 minutes, and the duration, C, of the second AC pulse is in the range of 15–45 minutes. The durations of the pulses are not critical; however, it has been noted that a duration of less than 5 minutes has virtually no effect on the patient's condition, while extending a pulse beyond 45 minutes provides no further improvement in the patient's condition. Generally, the duration of the second AC pulse exceeds the duration of the first AC pulse by 50%–100%. The strength of the first AC pulse is equal to the strength of the second AC pulse, in the preferred embodiment of the invention, the value of the magnetic strength being in a range of approximately 7.5–75 picotesia flux density. The strength of the magnetic field is approximately in the range of the human's brain electromagnetic activity detected with a SQUID magnetometer by Cohen in 1972 (Cohen (1972). "Magnetoencephalography: detection of the brain's electrical activity with a superconducting magnetometer." *Science,* 175, 664–666). While the strength of the magnetic fields may be varied from pulse to pulse, if desired, the strength of the magnetic fields has been maintained constant in the practice of the method because no difference in clinical response of the patient has been noticed for different values of the magnetic fields within the foregoing range. A typical value for the strength of the applied magnetic fields is 60 picotesia flux density. However, when the AC pulsed magnetic fields are applied over the temples through a transducer embedded in an earphone-like headset, their strength is higher reaching up to 1 microtesia flux density.

More specifically, in the case of a patient having Parkinson's disease, the second application is a combined AC/DC pulsed magnetic field of 15–45 minutes, C, while in the case of multiple sclerosis, the duration, C, which is a second AC pulsed magnetic field should be approximately 45 minutes. With respect to the AC frequency, in the case of multiple sclerosis, the first pulse frequency is 2 Hz–3 Hz and the second AC pulse frequency is 4 Hz–5.5 Hz, an increase of about 50%, For patients with Parkinson's disease, juvenile Parkinsonism, progressive supranuclear palsy, Shy-Drager syndrome, Huntington's chorea, AIDS dementia, motor neuron disease, essential tremor, ischemic stroke, diabetic neuropathy, macular degeneration, dystonia, tardive dyskinesia, Alzheimer's disease, migraine, depression, obsessive compulsive disorder, trichotillomania, posttraumatic stress disorder, impulsive aggressive behavior, chronic insomnia, sleep paralysis, bulimia, anxiety and panic disorder, and schizophrenia the first pulse frequency is 5 Hz and the second pulse frequency is 7 Hz–8.5 Hz, also an increase of approximately 50%. For an epileptic patient, the first pulse frequency is 4 Hz and the second pulse frequency is 7 Hz, also an increase of approximately 50%. For patients with traumatic spinal cord injuries and patients with autism, the first pulse frequency is 3–5 Hz and the second pulse frequency is 4–7 Hz, also an increase of approximately 50%. It is noted that the frequencies of stimulation employed for the multiple sclerosis patient as well as patients with traumatic spinal cord injuries and autism tend to be in proximity to the delta brain wave activity (range of delta activity: 0.5 Hz–3 Hz) measured by an electroencephalogram (EEG), and that the frequencies employed for the patient with Parkinson's disease, juvenile Parkinsonism, progressive supronuclear palsy, motor neuron disease, Huntington's chorea, AIDS dementia, Shy-Drager syndrome, essential tremor, diabetic neuropathy, ischemic stroke, macular degeneration, dystonia, tardive dyskinesia, Alzheimer's disease, migraine, epilepsy, depression, anxiety and panic disorder, obsessive compulsive disorder, trichotillomania, posttraumatic stress disorder, impulsive aggressive behavior, chronic insomnia, sleep paralysis, bulimia, substance abuse, and schizophrenia tend to be in proximity to the range of the theta brain wave activity (range of theta activity: 4 Hz–7 Hz).

The transmission of signals in the nervous system is such that within the neuron (nerve cell) transmission is accomplished by propagation of an electrical signal while between neurons signal propagation is accomplished via the mediation of a neurotransmitter. A neurotransmitter is a molecule, such as a molecule of serotonin, dopamine, acetyicholine, and histamine, or other neurotransmitter by way of example. During the propagation of an electrical signal the neurotransmitter is released from the transmitter neuron (presynaptic neuron) into the synaptic cleft from which it diffuses across the synaptic cleft to reach specific receptors in the receiving neuron (postsynaptic neuron). Activation of these receptors at the postsynaptic neuron causes either excitation or inhibition of the postsynaptic neuron. The transmitter neuron and the receiving receptor at the postsynaptic neuron are specific to only one type of neurotransmitter so that a plurality of different forms of the neuron transmitter/receptor allow for transmission of different forms of signals by respective ones of the neurotransmitter.

Neurotransmitters are produced in numerous locations throughout the nervous system. For instance, serotonin is produced in neurons that originate in the raphe nuclei of the brainstem and which project to numerous brain areas including the spinal cord, cerebellum, hypothalamus, limbic system, and cortex. In the central nervus system serotonin affects mood, behavior, sleep and arousal satiety, emesis, cardiovascular regulation, temperature control, motor control, cognition, pain, sedation, anxiety and depression. In the peripheral nervous system, the primary actions of serotonin are on the gastrointestinal tract and cardiovascular system, but it also affects the respiratory tract and genitourinary system. The neuroanatomical basis of these diverse behavioral effects of serotonin are related with the extensive and widespread innervation of the cerebral cortex, limbic system, brainstem and spinal cord by ascending and descending projections of serotonin neurons located in the brainstem raphe nuclei. It has been calculated that each projecting serotonin neuron sends over 500,000 terminals to the cerebral cortex. The average density of serotonin innervation in the cerebral cortex is substantially greater than that of other neurotransmitters including dopamine, acetylcholine and noradrenaline (Cowen (1991) "Serotonin receptor subtypes: implications for psychopharmacology." *British Journal of Psychiatry*, 159 (suppl. 12), 7–14; Fuller (1995) "Neural function of serotonin." *Scientific American* (Science & Medicine), 2, 48–57). It is now well established that melatonin is involved in the regulation of brain serotonin neurotransmission. The pineal gland affects a variety of metabolic, endocrine and behavioral functions through the mediation of serotonin neurons. While pinealectomy in rats has been shown to decrease serotonin levels in several brain regions, administration of melatonin increases brain serotonin concentrations. Dysfunction of the pineal gland may disrupt serotonin neurotransmission which is critical in spinal and supraspinal regulation of motor control as well as in regulation of sensory, autonomic, cognitive, and affective functions. In addition, serotonin plays an important role in the modulation of the immune system and in the integrity of the blood brain-barrier, disruption of which is thought to be a target of the pathological process of several neurodegenerative disorders.

It has been reported by patients who have been treated according to the present invention that they sense improvement in mood as well as motor and mental skills subsequent to the ingestion of the composition during the 4–8 weeks period preceding the initiation of magnetic treatment. These observations are in accordance with reports in the literature indicating that increased serotonin functions produce amelioration of symptoms of multiple sclerosis, Parkinson's disease, Alzheimer's disease, tardive dyskinesia, depression including seasonal afective disorder, migraine, and schizophrenia (Hyyppa et al., (1975) "Effect of L-tryptophan on central indoleamine metabolism and short-lasting neurologic disturbances in multiple sclerosis." *Journal of Neural Transmission*, 37, 297–304; Sano and Taniguchi (1972) "L-5-hydroxytryptophan (L-5-HTP) Therapie des Morbus Parkinson." *Munchen Medizinische Wochenschrift*, 114, 1717–1719; Meerwaldt (1986) "Treatment of hypokinetic rigid syndrome with fluvoxamine maleate." *Lancet*, 1, 977–978; Sandyk and Fisher (1989) "L-tryptophan supplementation in Parkinson's disease." *International Journal of Neuroscience*, 45, 215–219; McCance-Katz et al., (1992) "Serotonergic dysfunction in depression associated with Parkinson's disease." *Neurology*, 42, 1813–1814; Simpson and Foster (1986) "Improvement in organically disturbed behavior following trazodone treatment." *Journal of Clinical Psychiatry* 47, 192–193; Pinner and Rich (1988) "Effects of trazodone on aggressive behavior in seven patients with organic mental disorders." *American Journal of Psychiatry*, 145, 1295–1296; Sandyk et al., (1986) "L-tryptophan in drug-induced movement disorders with insomnia." *New England Journal of Medicine*, 314, 1257; Sandyk et al., (1988) "Efficacy of L-tryptophan in neuroleptic-induced tardive dyskinesia." *Neurology* (suppl 1), 38, 128; Kimball et al., (1960) "Effect of serotonin in migraine patients." *Neurology*, 10, 107–111; Asberg et al., (1986) "Therapeutic effects of serotonin uptake inhibitors in depression." *Journal of Clinical Psychiatry*, 46 (suppl. 4), 23–35; Levitt et al., (1991) "Tryptophan treatment and melatonin response in a patient with seasonal affective disorder." *Journal of Clinical Psychopharmacology*, 11, 74–75; Morand et al., (1983). "Clinical response of aggressive schizophrenics to oral tryptophan." *Biological Psychiatry*, 18, 575–577); Comings (1990) "Tourette syndrome and human behavior." (pp. 429–456), Duarte:CA: Hope Press).

Likewise, there have been also observations by patients of improvement in motor and mental functions upon receipt of only treatment with pulsed magnetic fields. However, the most dramatic improvements in motor functions and mental skills have been observed following treatment according to the present invention as described above.

With regards to the composition of the present invention, it is noted also that an increase of the concentration of serotonin in the brain cannot be accomplished by ingestion of the neurotransmitter serotonin since it does not pass from the blood into the brain (Wurtman and Fernstrom (1975) "Control of brain monoamine synthesis by diet and plasma amino acids." *The American Journal of Clinical Nutrition*, 28, 638–647). Therefore, any increase in the concentration of serotonin in the brain can be accomplished only by manufacture of serotonin within the brain. The aminoacid tryptophan or the immediate precursor of serotonin, 5-hydroxytryptophan (5-HTP), do cross from the blood into the brain. Therefore, L-tryptophan or L-5-HTP have been included in the composition, and are useful pharmacological strategies for elevation of brain's serotonin concentrations. Since in the pineal gland serotonin is converted to melatonin the administration of these serotonin precursors also enhances melatonin production.

The clinical response to the treatment is demonstrated by reference to FIGS. 1A–1C, 2A–2C and 3A–3D which are illustrative of successfull treatments using the present method.

Figure 1B:
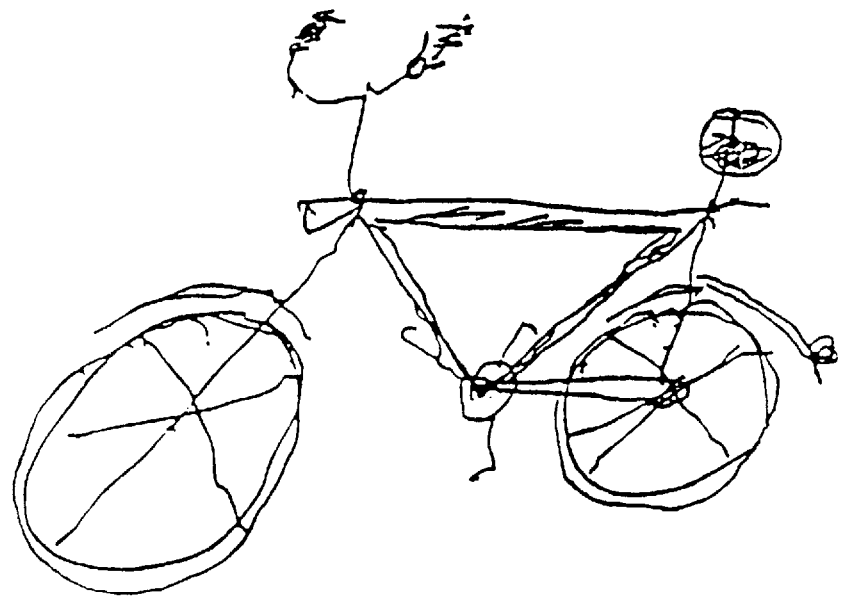

FIGS. 1A–C demonstrates the efficacy of externally applied AC magnetic fields in reversing the micrographia (small script) of a 69 year old patient having Parkinson's disease. For comparison purposes the drawings are presented without the use of the composition. FIG. 1A demonstrates the patient's drawing of a bicycle before magnetic treatment. Note the small size of the bicycle characteristic of the Parkinsonian micrographia. FIG. 1B shows the patient's drawing obtained 5 minutes after the application of the first pulsed magnetic treatment. Note the enlargement in the size of the bicycle. FIG. 1C shows the patient's drawing of the bicycle after 30 minutes of magnetic fields treatment composed of two 15-minute AC pulses of magnetic fields separated by a 15-minute break. Note the addition of details in the drawing as well as further enlargement of the size of the bicycle demonstrating reversal of the Parkinsonian micrographia.

The use of the foregoing procedure of administration of two 15-minute AC pulses of magnetic fields to give a total exposure of 30 minutes, wherein the two pulses are separated by a time interval in the range typically of 15 to 30 minutes, is employed also in the following examples.

Figure 2A:
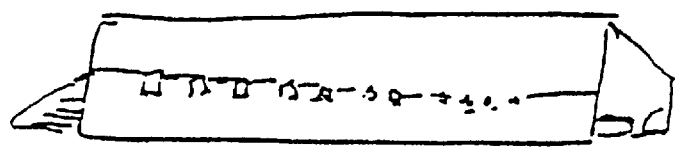
Figure 2B:
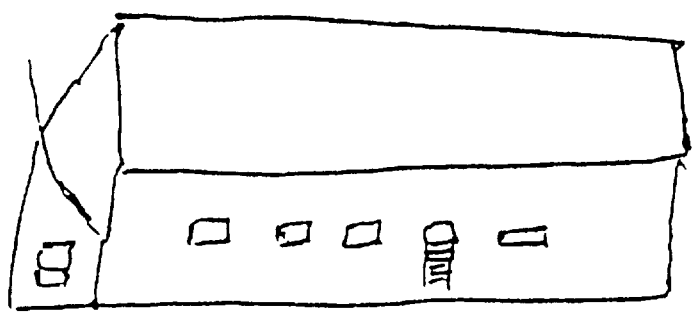

FIGS. 2A–C demonstrate the effect of pulsed magnetic fields on cognitive functions in a 70 year old mole patient afflicted with Alzheimer's disease of five years duration. FIG. 2A shows the patient's drawing of a house before magnetic treatment. Note the simplicity of the design, a pattern which is frequently seen in patients with Alzheimer's disease (Kirk and Kertesz (1991) "On drawing impairment in Alzheimer's disease." *Archives of Neurology*, 48, 73–77). FIG. 2B shows the patient's performance after 30 minutes of magnetic treatment (15 minutes of first AC pulse—break of 20 minutes—15 minutes of second AC pulse). FIG. 7C shows the patient's performance after 30 minutes of magnetic treatment (first AC pulse 15 minutes—break 15 minutes—second AC pulse 15 minutes) which was administered in conjunction with the composition as described herein before.

Figure 3A:
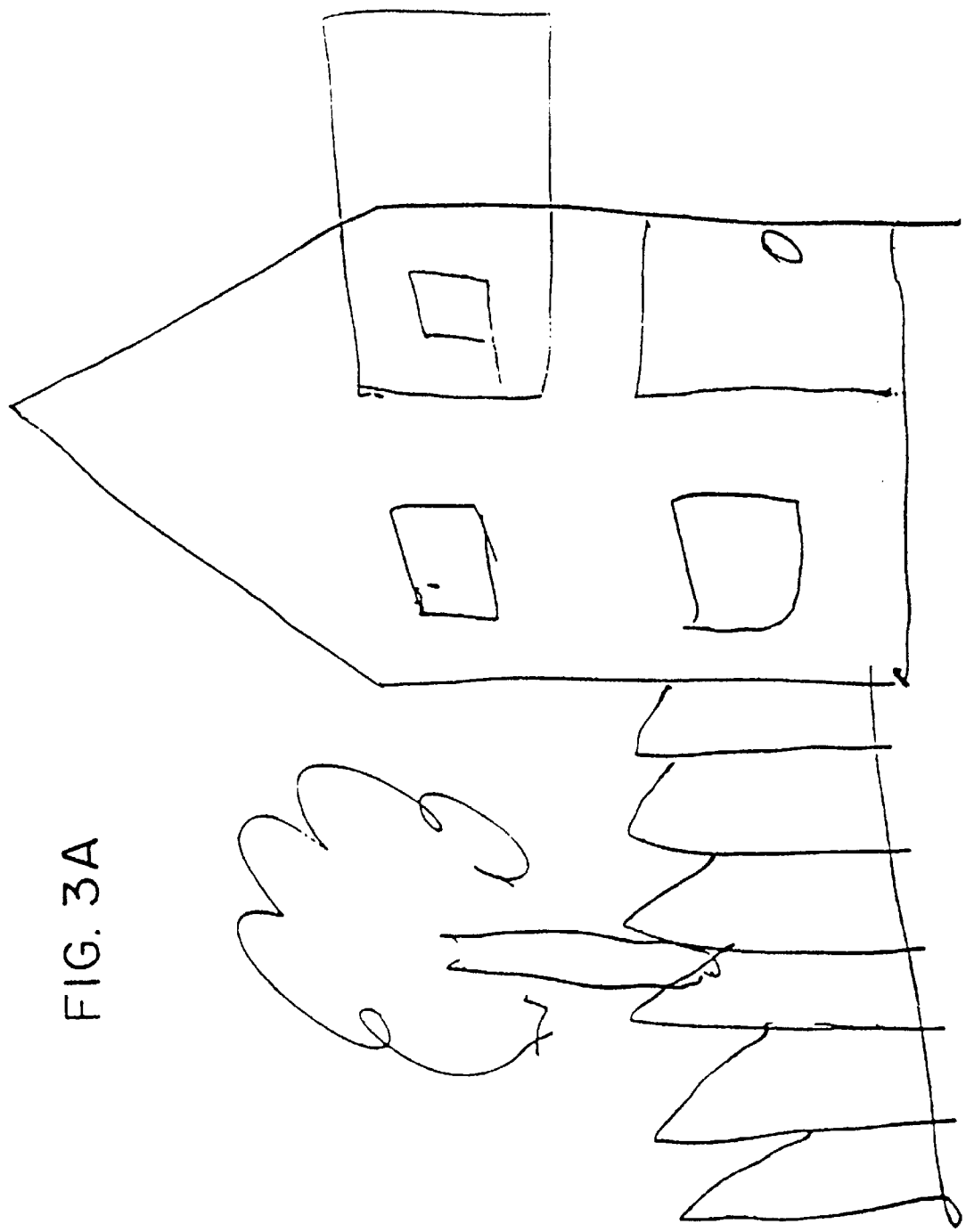
Figure 3C:
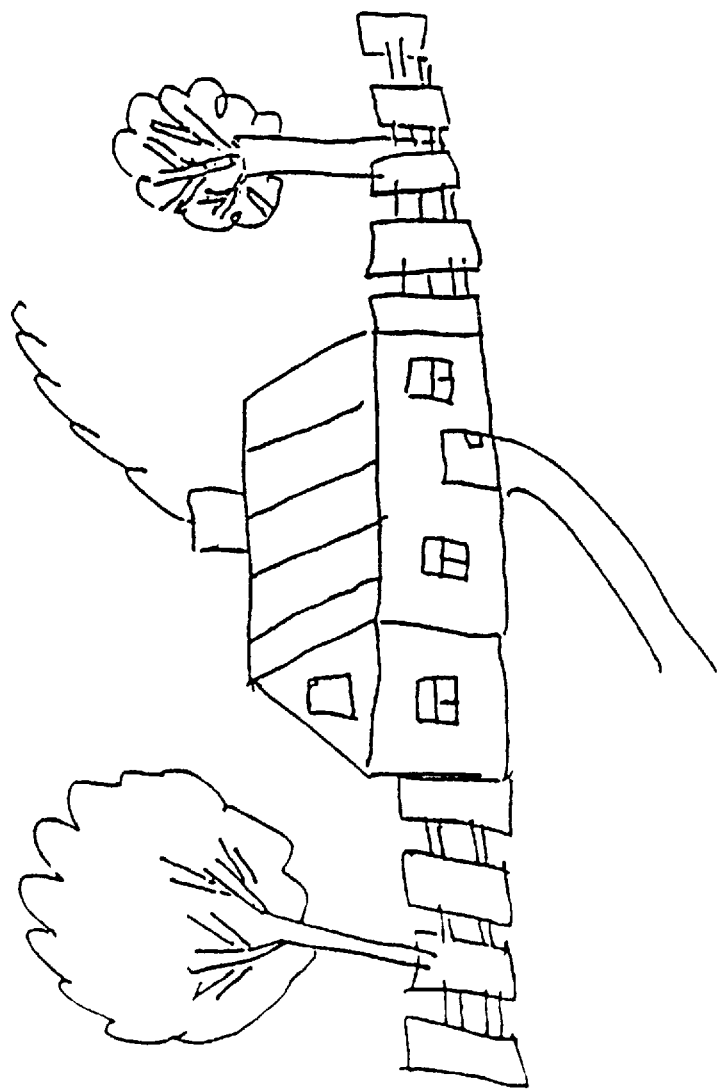
Figure 3D:
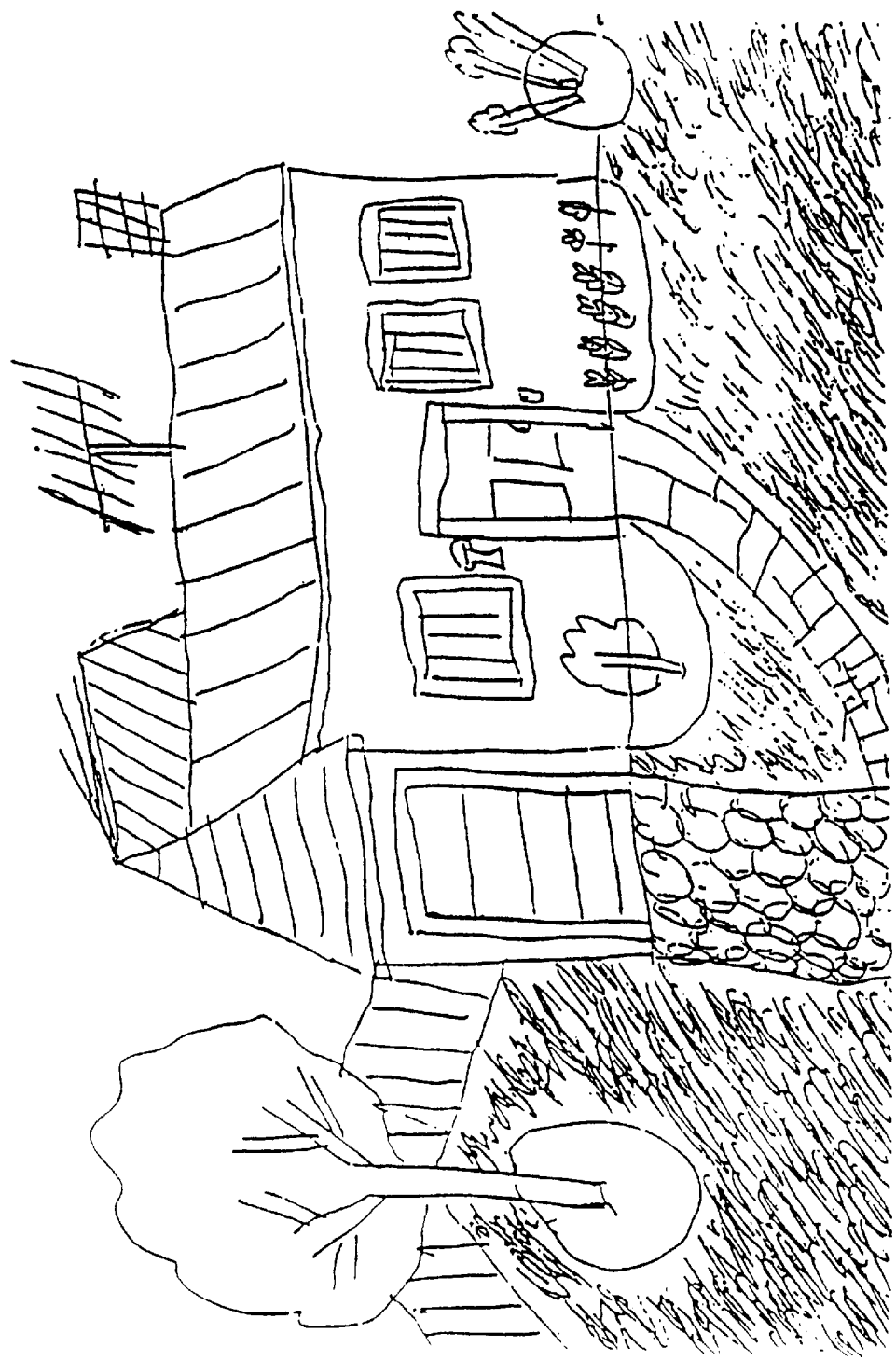

FIGS. 3A–3D demonstrate the effect of the treatment of the present invention on a 48 year old schizophrenic patient. FIG. 3A shows the patient's drawing of a house prior to the application of pulsed magnetic treatment. Note the simplicity of the design and poverty of perspectives. FIG. 3B shows the patient's drawing of a house after placebo treatment of 30 minutes. FIG. 3C shows the patient's drawing after application of pulsed magnetic treatment of 30 minutes duration (2 AC pulses of 15 minutes each). FIG. 3D shows the patient's performance when pulsed magnetic fields were applied in conjunction with the composition. Note the dramatic improvement in the perspectives of the drawing which included additional details.

Other and further uses and modifications of the method of the present invention will be more fully understood and appreciated by those skilled in the art by reference to the foregoing specification in the appended claims.

Figure 4A:

FIGS. 4A–C show attempts at a drawing by a 6½ year old child afflicted with Giles de la Tourette's syndrome wherein FIG. 4A shows an attempted drawing of the human figure prior to magnetic treatment which showed distortions, lack of perspectives and details, and abnormal presentation of the hands each having three projections for fingers. FIG. 4B shows the child's drawing of the human figure after two 15 minute AC pulses of magnetic treatment. Note improvement in perceptual organization with improved perspectives. FIG. 4C shows the child's drawing after treatment according to the present invention which comprised administration of the composition of the present invention followed by the application of two fifteen minute AC pulses of magnetic fields according to the present invention. Note further improvement in the perspectives of the drawing and the addition of details including facial expression.

Other and further uses of my composition and method of treatment will be more fully appreciated by those skilled in the art.

Figure 5A:
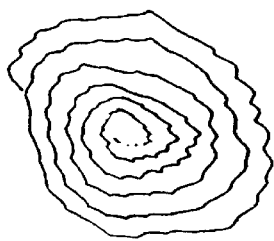
Figure 5B:
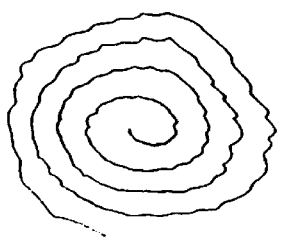
Figure 5C:
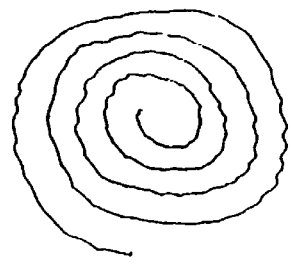

FIGS. 5A–C show attempts at a drawing of the Archimedes spirals by a patient afflicted with essential tremor wherein FIG. 5A shows an attempted drawing of the spirals with the right hand prior to magnetic treatment which demonstrates the tremor. Also, note the impact of tremor on the patient's signature and date of study, FIG. 5B shows an attempted drawing of the spirals following application of AC pulsed magnetic fields of 15 minutes duration employing a 5 Hz sinusoidal wave with a 50% amplitude modulation. Note reduction in the severity of the tremor and the improvement in patient's signature and date of the study. FIG. 5C shows an attempted drawing of the spirals following application of the second AC pulsed magnetic treatment of 30 minute duration employing a 7 Hz sinusoidal wave with a 50% amplitude modulation wherein the second AC pulse has been administered after a 30 minute interval according to the present invention.

Figure 6A:
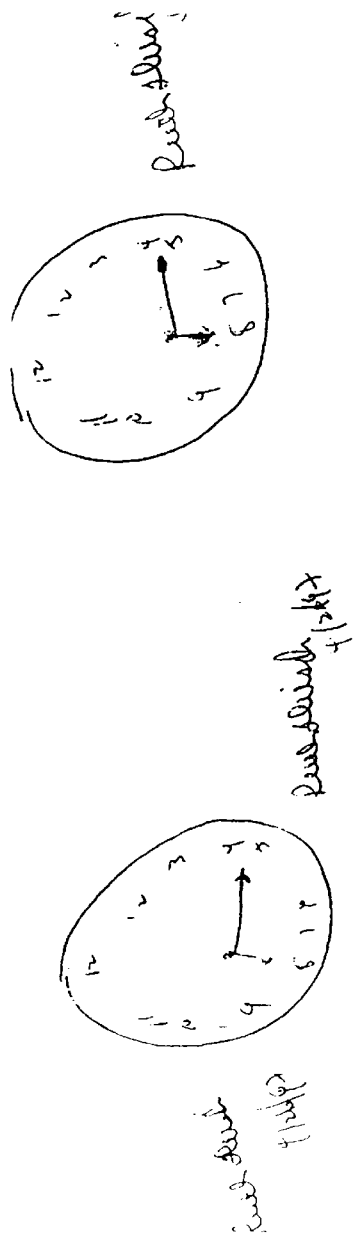
FIGS. 6A–C show spontaneous drawings by a 67 year old woman afflicted with progressive supranuclear palsy (PSP), a disorder which is characterised by a Parkinsonian-like syndrome associated with intellectual deterioration.
Figure 6B:
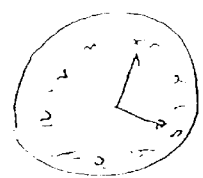
Figure 6C:

FIGS. 6A–C show spontaneous drawings by a 67 year old woman afflicted with progressive supranuclear palsy (PSP), a disorder which is characterised by a Parkinsonian-like syndrome associated with intellectual deterioration. FIG. 6A shows an attempted drawing of a clock, bicycle, and a house prior to magnetic treatment. Note the small size of the drawing of the bicycle and house reflecting the micrographia (small script) of Parkinsonism. FIG. 6B shows the patient's drawings after a single AC pulsed magnetic treatment of 15 minute duration employing a 5 Hz sinusoidal wave. Note the immediate increase in the size of the drawings and the presentation of a more elaborate house. FIG. 6C shows the patient's drawings after the application of a second sinusoidal AC pulsed magnetic field of 7.5 Hz frequency wherein the second pulse has been administered after a 15 minute interval according to the present invention. Note further increase in the size of the drawings and the detailed presentation of the house.

Figure 7A:
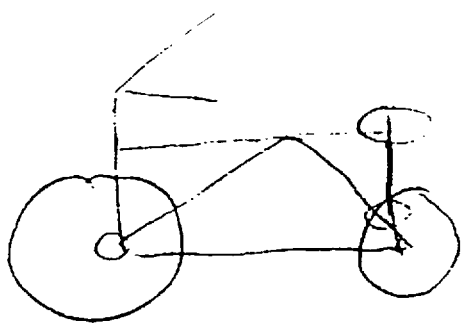
FIGS. 7A–C show spontaneous drawings of a bicycle by a 48 year-old man afflicted with juvenile Parkinsonism with onset of first symptoms at the age of 40.
Figure 7B:
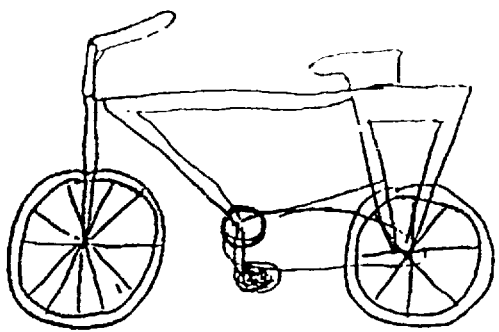
Figure 7C:
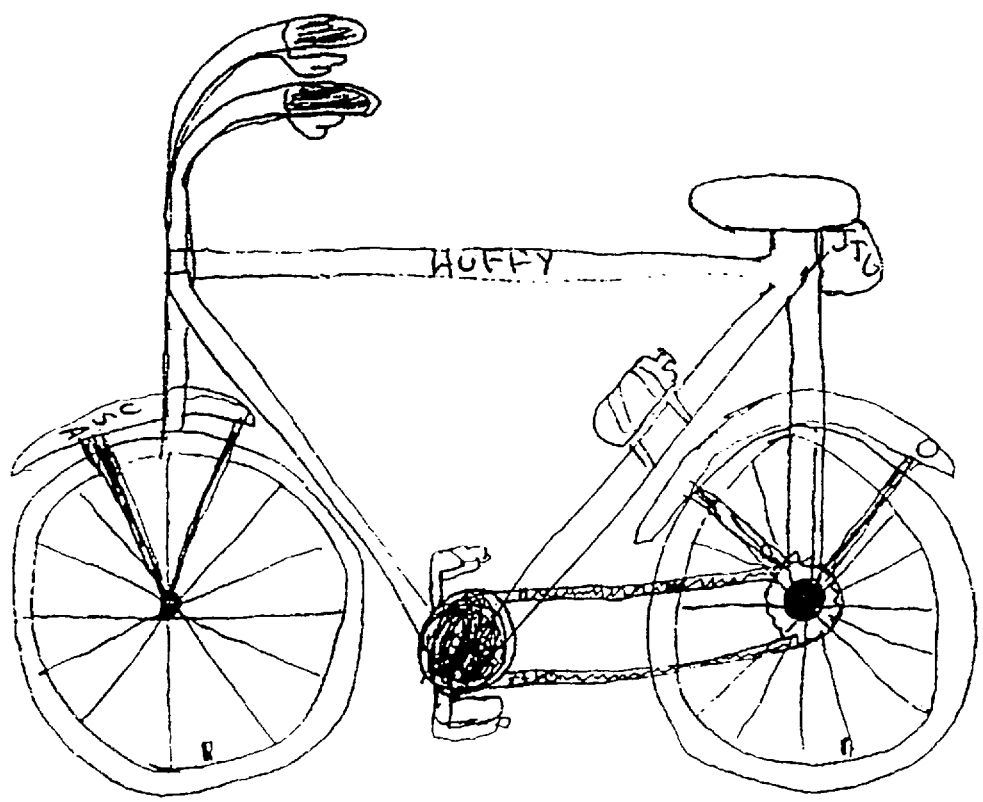

FIGS. 7A–C show spontaneous drawings of a bicycle by a 48 year-old man afflicted with juvenile Parkinsonism with onset of first symptoms at the age of 40. FIG. 7A demonstrates the patient's drawing of a bicycle before magnetic treatment. Note the small size of the bicycle characteristic of the Parkinsonian micrographia. In addition, note the lack of essential details in the bicycle such as the drive chain, pedals, and spokes as well as the improper position of the seat and the differences in the size of the wheels with the front wheel being twice the size of the rear wheel. FIG. 7B shows the patient's drawing of a bicycle after 40 minutes of magnetic treatment composed of two 20-minute AC pulses of magnetic fields separated by a 15-minute interval. The AC frequency of the first treatment was 5 Hz and that of the second treatment was 7.5 Hz using a square wave in both applications. Note the increase in the size of the bicycle and the inclusion of additional details such as spokes, a drive chain and pedals. FIG. 7C shows the patient's spontaneous drawing of a bicycle three months later during which time he received weekly treatments with magnetic fields which were applied in conjunction with the composition. Note the dramatic increase in the size of the bicycle indicating reversal of the Parkinsonian micrographia. In addition, note the detailed demonstration of the bicycle indicating improvement in mechanical reasoning and visuographic skills.

Figure 8A:
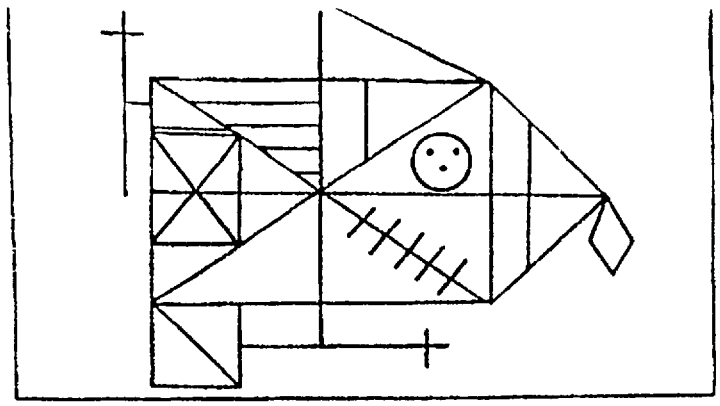
FIGS. 8A–C show the effect of treatment with AC pulsed magnetic fields on cognitive functions in a 36 year-old man with AIDS dementia. Patient was instructed to view the Rey Complex Figure (FIG. 8A) for one minute and five minutes later attempt to recall the Figure from memory.
Figure 8B:
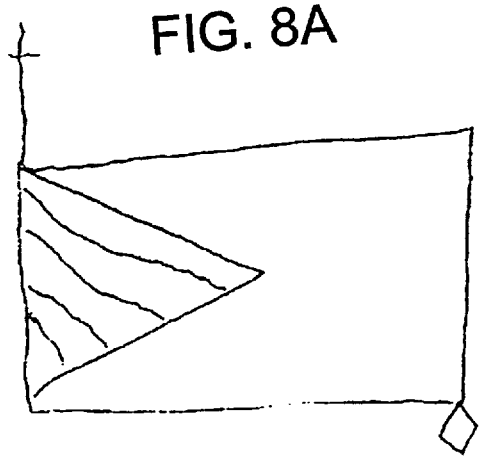
Figure 8C:
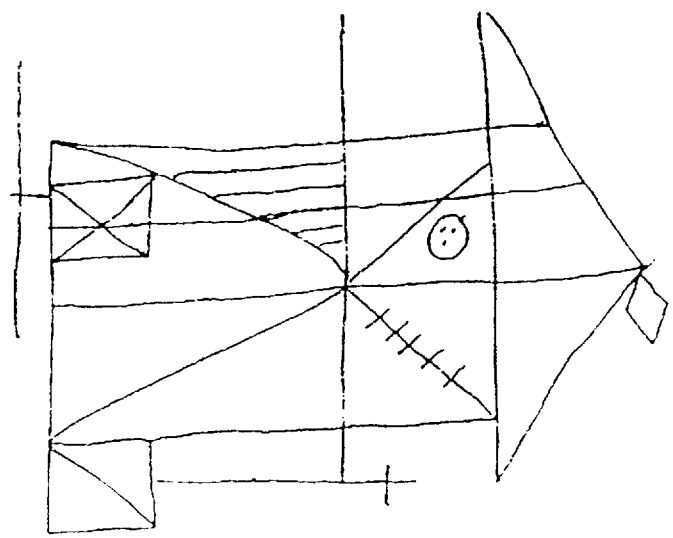

FIGS. 8A–C show the effect of treatment with magnetic fields on cognitive functions in a 36 year-old man with AIDS dementia. Patient was instructed to view the Rey Complex Figure (FIG. 8A) for one minute and five minutes later attempt to recall the Figure from memory. FIG. 8B shows the patient's attempt to recall the Figure prior to magnetic treatment demonstrating an almost 100% degradation of details reflecting poor visual memory related to right temporal lobe dysfunction. FIG. 8C shows the patient's attempt to recall the Rey Complex Figure 4 weeks later during which time he received twice weekly treatment with magnetic fields according to the present invention. A treatment comprised two successive applications of AC pulsed magnetic fields each of 20 minutes separated by an interval of 15 minutes. The AC pulsed frequency of the first treatment was 5 Hz and of the second treatment 7 Hz using a sinusoidal wave. Note the dramatic increase in his ability to recall the Figure indicating marked improvement in visual memory.

I claim:

1. A method of treating neurological and mental disorders which are associated with and related pathogenetically to deficient serotonin transmission and impaired pineal melatonin functions in humans and for treating neurological and mental disorders which are associated with or related pathogenetically to deficient serotonin neurotransmission and impaired pineal melatonin functions in humans which comprises administering to a human in need thereof an effective amount of a composition which increases serotonin transmission to the human to be treated followed by the application to the brain of the human of a sufficient amount of an AC pulsed magnetic field alone, or in combination with a DC magnetic field and low frequency random noise, of proper intensity, frequency, waveform, wave symmetry and phase shift of the wave to treat the disorder.

2. A method according to claim 1 which further comprises having the human consume a sufficient amount of a dietary composition which will increase plasma tryptophan concentrations beginning prior to the application of the magnetic field.

3. A method according to claim 1 for the treatment of juvenile Parkisnonism wherein the AC pulsed frequency is 5-Hz–8.5 Hz.

4. A method according to claim 1 for the treatment of progressive supranuclear palsy wherein the AC pulsed frequency is 5 Hz–8 Hz.

5. A method according to claim 1 for the treatment of motor neuron disease (amyotrophic lateral sclerosis) wherein the AC pulsed frequency is 5 Hz–8 Hz.

6. A method according to claim 1 for the treatment of essential tremor wherein the AC pulsed frequency is 5 Hz–8 Hz.

7. A method according to claim 1 for the treatment of Huntington's chorea wherein the AC pulsed frequency is 5 Hz–8 Hz.

8. A method according to claim 1 for the treatment of AIDS dementia wherein the AC pulsed frequency is 5 Hz–8 Hz.

9. A method according to claim 1 for the treatment of Shy-Drager syndrome wherein the AC pulsed frequency is 5 Hz–8 Hz.

10. A method according to claim 1 for the treatment of traumatic spinal cord injuries wherein the AC pulsed frequency is 3 Hz–7 Hz.

11. A method according to claim 1 for the treatment of ischemic stroke wherein the AC pulsed frequency is 5 Hz–8 Hz.

12. A method according to claim 1 for the treatment of autism wherein the AC pulsed frequency is 3 Hz–7 Hz.

13. A method according to claim 1 for the treatment of macular degeneration wherein the AC pulsed frequency is 5 Hz–7 Hz.

14. A method according to claim 1 for the treatment of diabetic neuropathy wherein the AC pulsed frequency is 5 Hz–7 Hz.

15. A method according to claim 1 for the treatment of alcohol dependency wherein the AC pulsed frequency is 5 Hz–7 Hz.

16. A method according to claim 1 for the treatment of trichotillomania wherein the AC pulsed frequency is 5 Hz–7 Hz.

17. A method according to claim 1 for the treatment of posttraumatic stress disorder wherein the AC pulsed frequency is 5 Hz–8 Hz.

18. A method according to claim 1 for the treatment of impulsive aggressive behavior wherein the AC pulsed frequency is 5 Hz–8 Hz.

19. A method according to claim 1 for the treatment of chronic insomnia wherein the AC pulsed frequency is 5 Hz–8 Hz.

20. A method according to claim 1 for the treatment of sleep paralysis wherein the AC pulsed frequency is 5 Hz–7 Hz.

21. A method according to claim 1 for the treatment of bulimia wherein the AC pulsed frequency is 5 Hz–8 Hz.

22. A method according to claim 1 for the treatment of multiple sclerosis wherein the amplitude of the AC pulsed magnetic field is modulated at a range of 25%–100%.

23. A method according to claim 1 for the treatment of multiple sclerosis wherein the frequency of the AC pulsed magnetic field is modulated at a range of 10%–50%.

24. A method according to claim 1 for the treatment of multiple sclerosis wherein the shape of the waveform of the AC pulsed magnetic field is symmetric or asymmetric.

25. A method according to claim 1 for the treatment of multiple sclerosis wherein the AC pulsed magnetic field is combined with a DC magnetic field.

26. A method according to claim 1 for the treatment of multiple sclerosis wherein random noise of proper frequency is combined with the AC pulsed magnetic field.

27. A method according to claim 1 for the treatment of multiple sclerosis wherein the magnetic field is administered over the temples in a form of a two-phase AC pulsed sinusoidal wave with a phase shift ranging from 0° to 180°.

28. A method according to claim 1 for the treatment of multiple sclerosis wherein the AC pulsed magnetic field is applied simultaneously over both temples or alternating from side to side at an interval of 5 to 30 seconds.

29. A method according to claim 1 for the treatment of juvenile Parkinsonism wherein the AC pulsed magnetic field is a time varying field with a waveform which is square.

30. A method according to claim 1 for the treatment of Gilles de la Tourette's syndrome wherein the AC pulsed magnetic field is combined with random noise of proper frequency.

31. A method according to claim 1 wherein the stimulant of serotonin receptors is ergoloid mesylates, pergolide mesylate, or buspirone.

32. A method according to claim 1 wherein the composition includes a stimulant of serotonin synthesis which is vitamin B1, vitamin B3, vitamin B6, blotin, S-adenosyl methionine, vitamin D, folic acid, ascorbic acid, magnesium, coenzyme $Q_{10}$, piracetam, or mixtures of two or more thereof.

33. A method according to claim 1 wherein the composition includes the serotonin re-uptake inhibitor which is sertraline, nefazodone, trazodone, fluoxetine or a mixture thereof.

34. A method according to claim 2 wherein the dietary composition comprises tryptophan rich foods.

35. A method according to claim 34 wherein the tryptophan rich foods are turkey, milk, bananas, nuts, and sunflower seeds.

36. A method according to claim 35 for the treatment of motor neuron disease, autism, alcohol dependency and post-traumatic stress syndrome wherein 4 oz. of turkey twice a week, 8 oz. of milk per day, 1 banana per day, 1–2 oz. of nuts per day and 3–4 oz. of sunflower seeds per day consumed by the human.

37. A method according to claim 1 wherein the AC pulsed magnetic fields are applied to the brain of the human using a helmet-like transducer array.

38. A method according to claim 37 wherein the helmet-like transducer array comprises an array of coils which are flat or helical.

39. A method according to claim 1 wherein the AC pulsed magnetic fields are applied to the brain of the human through a transducer embedded in an earphone-like headset.

40. A method according to claim 39 wherein the transducer is comprised of 3 solenoid-like coils which are connected in parallel.

41. A method according to claim 40 wherein the AC pulsed magnetic fields are applied to the brain over the temples.

42. A method according to claim 41 wherein the strength of the AC pulsed magnetic field is in the range of 7.5 picotesia to 1 microtesia flux density.

43. A method according to claim 1 wherein the AC pulsed magnetic field is a time varying field with a waveform which is sinusoidal, triangular, trapezoidal, square, sawtooth or a composite thereof, dependent upon the condition to be treated.

44. A method according to claim 1 wherein the composition which increases serotonin transmission comprises an effective amount of a serotonin precursor, an effective amount of a stimulant to increase plasma tryptophan concentrations, an effective amount of a stimulant to facilitate the transport of tryptophan into the brain of the human, an effective amount of a stimulant of serotonin synthesis, an effective amount of a serotonin reuptake inhibitor, an effective amount of a stimulant of serotonin release and an effective amount of a stimulant of serotonin receptors.

45. A method according to claim 43 wherein the serotonin precursor is selected from the group consisting of L-tryptophon or L-5-hydroxytryptophan; the stimulant to increase plasma tryptophan concentrations is a salicylate; the stimulant to facilitate the transport of tryptophon into the brain is selected from the group consisting of vitamin B3 and chromium; the stimulant of serotonin synthesis is selected from the group consisting of vitamin B1, vitamin B3, vitamin B6, biotin, S-adenosylmethionine, vitamin D, folic acid, ascorbic acid, magnesium, coenzyme Q10 and piracetam; the serotonin reuptake inhibitor is selected from the group consisting of sertraline, nefazodone, fluoxetine and trazodone; the stimulant of serotonin release is fenfluramine; and the stimulant of serotonin receptor is selected from the group consisting of ergolold mesylate, pergolide mesylate, and buspirone.

* * * * *